United States Patent
Creamer et al.

(10) Patent No.: US 7,160,970 B2
(45) Date of Patent: *Jan. 9, 2007

(54) PROCESS FOR MANUFACTURING POLYMERS

(75) Inventors: Marianne Patricia Creamer, Warrington, PA (US); Lester William Greene, Jr., Willow Grove, PA (US); Ari Kenneth Kar, Warrington, PA (US); Miao Wang, Horsham, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/943,317

(22) Filed: Sep. 17, 2004

(65) Prior Publication Data

US 2005/0107546 A1    May 19, 2005

Related U.S. Application Data

(60) Provisional application No. 60/520,785, filed on Nov. 17, 2003.

(51) Int. Cl.
*C08F 20/56* (2006.01)

(52) U.S. Cl. .................. 526/287; 526/288; 526/303.1; 526/304; 526/318.5; 526/329.7; 525/328.5; 525/329.4

(58) Field of Classification Search ............. 526/287, 526/288, 303.1, 304, 307.6, 318.5, 329.7; 525/329.4, 328.5
See application file for complete search history.

(56) References Cited

U.S. PATENT DOCUMENTS

| | | | |
|---|---|---|---|
| 4,401,650 A | | 8/1983 | Salamone |
| 4,427,836 A | | 1/1984 | Kowalski et al. |
| 4,469,825 A | | 9/1984 | Kowalski et al. |
| 4,578,267 A | | 3/1986 | Salamone |
| 4,594,363 A | | 6/1986 | Blankenship et al. |
| 4,677,003 A | | 6/1987 | Redlich et al. |
| 4,859,458 A | * | 8/1989 | Salamone et al. ....... 424/70.15 |
| 4,910,229 A | | 3/1990 | Okubo |
| 4,973,409 A | | 11/1990 | Cook |
| 5,157,084 A | | 10/1992 | Lee et al. |
| 5,521,266 A | | 5/1996 | Lau |
| 5,663,213 A | | 9/1997 | Jones et al. |
| 6,225,429 B1 | * | 5/2001 | Chuang et al. ............. 526/264 |
| 6,384,104 B1 | | 5/2002 | Chang et al. |
| 6,569,413 B1 | * | 5/2003 | Hessefort et al. ........ 424/70.11 |

FOREIGN PATENT DOCUMENTS

| | | |
|---|---|---|
| EP | 0331421 | 9/1989 |
| EP | 0267726 | 5/1993 |
| EP | 0915108 | 5/2003 |
| EP | 1488774 A | 12/2004 |

* cited by examiner

*Primary Examiner*—Roberto Rabago

(57) ABSTRACT

The present invention is directed to methods for preparing multi-functional emulsion polymers.

1 Claim, No Drawings

PROCESS FOR MANUFACTURING POLYMERS

CROSS REFERENCE TO RELATED PATENT APPLICATIONS

This is a non-provisional patent application of co-pending U.S. provisional patent application Ser. No. 60/520,785 filed Nov. 17, 2003.

The present invention relates to polymers useful for treating and modifying hair. More particularly, this invention is directed to a process that incorporates small amounts of one or more acid-containing monomers in solution polymers. The invention also provides a hybrid process for preparing the solution polymers, combining gradual addition and shot addition of monomers used to prepare such polymers.

Polymers incorporated in hair fixatives do not provide an adequate balance between conflicting requirements of a water resistant/water insensitive character for good curl retention at high levels of moisture and humidity versus hygroscopic/water sensitive character for rapid and complete removal of the polymer from hair when rinsed with water. Most hair fixative polymers were designed to be soluble in alcohol or propellants, and typically such polymers have poor solubility in water. Polymer performance as a fixative, however, is also affected (typically an adverse or detrimental interaction) when water is incorporated into a hair fixative formulation. Examples which illustrate such an imbalance are cationic polymers such as polyquaternium-11 and polyquaternium-4. The cationic polymers are excellent film-forming polymers, but their high substantivities to hair make them difficult to wash out of hair treated with such polymers. Consequently, anionic and non-ionic polymers are most frequently used as hair fixatives. However, such polymers also have disadvantages associated with their use as hair fixatives. Anionic hair fixative polymers, for example, because of their high solubility in water are also considered too hygroscopic and often exhibit poor hair setting properties in high humidity environments.

U.S. Pat. No. 6,569,413 B1 discloses a cosmetically acceptable fixative composition comprising from 0.1 to about 10 weight percent, based on polymer solids, of an anionic polymer, wherein the anionic polymer is composed of from 10 to 80 mole percent of 2-acrylamido-2-methyl-1-propanesulfonic acid or a base addition salt thereof and from 90 to 20 mole percent of one or more anionic or non-ionic monomers and a method of setting hair using the anionic polymer composition. The process used to prepare the polymers is a conventional solution polymerization. However, the conventional solution process limits the types of polymer composition that can be prepared and in turn limits polymers ability to treat hair, attempt to balance the conflicting requirements of water-resistance for good curl retention at high humidity versus water-sensitivity for rapid and complete removal of the polymer from hair when rinsed with water. In addition, polymers prepared by conventional methods lose clarity when formulated in hair treatments (e.g. including hair fixatives, hair conditioners) and have poor compatibility with certain thickeners including polycarboxylic acids and carbomers, resulting in lowered and/or unstable formulation viscosities. The polymers also have undesirable humidity resistance, undesirable hair modification properties including modifying hair texture to provide the user a raspy rather than silky feeling as to hair texture and polymer flaking issues after deposition on hair. It is therefore desirable to use new methods to prepare polymers having the proper balance of properties for treating and modifying hair.

Inventors provide a new process for preparing multi-functional polymers that are useful for modifying hair. The invented polymers have an excellent balance of water resistance versus water sensitivity, good color stability and good water stability, the polymers are non-flaking after application to hair, polymers are compatible when combined with additives including neutralizers, surfactants and thickeners. The polymers produced from the method exhibit unexpected clarity, exhibit stable viscosities when combined with one or more additives in formulations and are not dependent either on a particular neutralizing agent or a sequence of combination with additives when the polymers are formulated. The polymers of the invention are used to prepare hair formulations that are clear and non-hazy and hair formulations that have stable viscosities over time and are compatible with formulation additives including neutralizers, surfactants and thickeners, including polycarboxylic acids (e.g. poly(acrylic acid) pAA) and carbomers (e.g Carbopol™ available from B.F. Goodrich). Inventors discovered that the compatibility problem with certain rheology modifiers, the problem of clarity of the polymers in formulations and the formulation viscosity stability problem, all associated with anionic solution polymers known from the prior art and described above, are solved by successfully including small amounts of one or more acid-containing monomers in solution polymers of the present invention. Addition of small amounts of one or more acid-containing monomers to the invented solution polymers unexpectedly improves the clarity of such polymers in formulations. Moreover, addition of small amounts of acid-containing monomers to certain copolymers known in the art also unexpectedly improves the clarity of such polymers in formulations. Polymers of the invention, including selected copolymers, terpolymers, tetrapolymers and other solution polymers incorporating a plurality of monomers have unique properties which cannot be attained in anionic solution copolymers taught in the prior art, including acrylamide/2-acrylamido-2-methyl-1-propanesulfonic acid (AM/AMPS™, AMPS™ is available from Lubrizol Corp.) and methacrylic acid/2-acrylamido-2-methyl-1-propanesulfonic acid (MAA/AMPS™) copolymers. The inventors provide a process for preparing the polymers and a process for incorporating the solution polymers of the invention into compositions and formulations including those used in personal care, cosmetic, consumer, and pharmaceutical products for treating and modifying mammalian skin and hair.

The invention provides a process for preparing a polymer composition comprising the step of: (a) preparing a copolymer comprising, as polymerized monomer units, (i) 50 to 89.9 weight percent of one or more ethylenically unsaturated monomers and (ii) 10 to 40 weight percent of 2-acrylamido-2-methyl-1-propanesulfonic acid and salts thereof, by varying the feeds of monomers (i) and (ii) with respect to time and each monomer prior to neutralizing the polymer with a base. According to a separate embodiment, the polymers are prepared used a gradual addition of monomers.

The invention provides a process for preparing a multi-functional polymer composition comprising the step of: (a) preparing a polymer comprising, as polymerized monomer units (i) 50 to 89 weight percent of one or more ethylenically unsaturated monomers, (ii) 10 to 40 weight percent of 2-acrylamido-2-methyl-1-propanesulfonic acid and salts thereof and (iii) 1 to 30 weight percent of one or more acid-containing ethylenically unsaturated monomers; by a hybrid feed that further comprises combining gradual addition and shot addition of monomers used to prepare the polymer.

The invention provides a process for preparing a multifunctional hair modifying formulation comprising the steps of: (a) providing one or more polymers comprising, as polymerized monomer units (i) 50 to 89 weight percent of one or more ethylenically unsaturated monomers, (ii) 10 to 40 weight percent of 2-acrylamido-2-methyl-1-propanesulfonic acid and salts thereof and (iii) 1 to 30 weight percent of one or more acid-containing ethylenically unsaturated monomers; and (b) one or more additives, wherein the polymer is compatible in the one or more additives, including thickeners, rheology modifiers, other hair fixative polymers, other polymers, neutralizers, humectants, surfactants, conditioning agents, silicones, colors, dyes, fragrances, naturally occurring materials and preservatives; and wherein the polymer can be neutralized at any stage of preparing the formulation.

The invention also provides a process for treating and modifying hair comprising the steps of applying to hair a polymer composition comprising, as polymerized monomer units (i) 50 to 89 weight percent of one or more ethylenically unsaturated monomers; (ii) 10 to 40 weight percent of 2-acrylamido-2-methyl-1-propanesulfonic acid and salts thereof, and (iii) 1 to 30 weight percent of one or more acid-containing ethylenically unsaturated monomers; wherein the polymer is combined with one or more additives, including thickeners, rheology modifiers, other hair fixative polymers, other polymers, neutralizers, humectants, surfactants, conditioning agents, silicones, colors, dyes, fragrances, naturally occurring materials and preservatives to prepare a hair formulation; wherein the polymer is compatible in the one or more additives and wherein the polymer can be neutralized at any stage of preparing the formulation.

"Anionic monomer" refers to a monomer as defined herein which possesses a net negative charge above a certain pH value. Representative anionic monomers include base addition salts of acrylic acid, methacrylic acid, itaconic acid, maleic acid 2-acrylamido-2-methyl-1-propanesulfonic acid, sulfopropyl acrylate or methacrylate or other water-soluble forms of these or other polymerizable carboxylic or sulfonic acids, sulphomethylated acrylamide, phosphoethyl(meth)acrylamide, allyl sulphonate, styrene sulfonic acid, sodium vinyl sulphonate, and the like.

"Monomer" refers to any ethylenically unsaturated group, including polyethylenically unsaturated groups of a compound including allylic, vinylic and acrylic groups. The monomer may be anionic, cationic or non-ionic. The term "other" monomers includes additional anionic, cationic, non-ionic and hydrophobic monomers used to prepare polymers of the invention. The term "hydrophobic" refers to monoethylenically unsaturated monomers which have low water solubility under the conditions of emulsion polymerization, as described in U.S. Pat. No. 5,521,266.

"Non-ionic monomer" refers to a monomer as defined herein which is electrically neutral. Representative non-ionic, water-soluble monomers include acrylamide, methacrylamide, N,N-dimethylacrylamide, N,N-diethylacrylamide, N-isopropylacrylamide, N-vinylformamide, N-vinylmethylacetamide, N-vinyl pyrrolidone, hydroxyethyl methacrylate, hydroxyethyl acrylate, hydroxypropyl acrylate, hydroxypropyl methacrylate, t-butylacrylamide, N-methylolacrylamide, alkyl(meth)acrylates such as methyl (meth)acrylate, butyl acrylate and ethylacrylate, vinyl monomers such as ethylene, styrene, divinylbenzene, di-isobutylethylene, vinyl acetate and N-vinyl pyrolidone, and allyl monomers such as allyl(meth)acrylate. "Cationic monomer" refers to a monomer as defined herein which possesses a net positive charge below a certain pH value. Representative cationic, water-soluble monomers include quaternary ammonium salts of amine functionalized monomers such as acrylamide, methacrylamide, N,N-dimethylacrylamide, N,N-diethylacrylamide, N-isopropylacrylamide, N-vinylformamide, N-vinylmethylacetamide, N-vinyl pyrrolidone, t-butylacrylamide, N-methylolacrylamide, tributylammonium ethyl(meth)acrylate TBAEMA, DMAEMA, DMAPMAM, diallyldimethylammonium chloride DADMAC, methylacrylamidopropyltrimethylammonium chloride MAPTAC, acrylamidopropyltrimethylammonium chloride APTAC, N-vinyl pyrolidone, polyquaternium-11 and polyquaternium-4.

The term "acid-containing monomer refers to ethylenically unsaturated monomers containing carboxylic acid, phosphonic acid, phosphinic acid, sulfinic acid and sulfonic acid groups. Suitable examples include (meth)acrylic acid, maleic acid, succinic acid, itaconic acid, vinyl phosphonic acid and vinylsulfonic acid.

As used herein, the term "salts" refers to the ionic salt resulting from reaction of a carboxylic acid, phosphonic and sulfonic group ($-C(O)OH$, $-P(O)OH$, $-S(O)OH$)) with a base. Suitable bases include alkali metal, alkali earth metal, metal and quaternary ammonium hydroxides, carbonates and bicarbonates; ammonia; primary, secondary and tertiary organic amines. Representative alkali, alkaline earth and metal salts include lithium, sodium, potassium, calcium, magnesium and zinc. Suitable amines include methylamine, ethylamine, ethoxylated amines, diethylamine, triethylamine, pyridine, piperdine, ethanolamine, piperazine, aminoethylpropanol, ethanolamine, diethanolamine triethanolamine. The term "salts" also refers to the ionic salt resulting from reaction of an amine ($-NH_2$), including amides ($-CONH_2$) with an acid. Suitable acids include hydrochloric acid, phosphoric acid, phosphonic acids acetic acid, (meth)acrylic acid, citric acid, sulfonic acids and sulfuric acid.

As used herein, the term "copolymer" refers to polymer compositions containing units of two or more different monomers, the term "terpolymer" refers to polymer compositions containing units of three or more different monomers, and the term "tetrapolymer" refers to polymer compositions containing units of four or more different monomers. A plurality of suitable monomer units is usefully employed in accordance with the invention.

As used herein, the following terms have the designated definitions, unless the context clearly indicates otherwise. The term "alkyl (meth)acrylate" refers to either the corresponding acrylate or methacrylate ester; similarly, the term "(meth)acrylic" refers to either acrylic or methacrylic acid and the corresponding derivatives, such as esters or amides. All percentages referred to will be expressed in weight percent (%), based on total weight of polymer or composition involved, unless specified otherwise. The following abbreviations are used herein: g=grams; ppm=parts per million by weight/volume. Unless otherwise specified, ranges listed are to be read as inclusive and combinable and temperatures are in degrees centigrade (° C.).

As used herein the term "hybrid feed" refers to a process of addition of one or monomers that combines conventional shot addition and gradual addition of monomers to a polymerization reaction over time.

Polymers of the present invention typically have a weight average molecular weight ($M_w$) for the backbone polymer of 200 to 800,000, including from 2,000 to 300,000 and from 200,000 to 300,000. Weight average molecular weights for the backbone polymer are based on aqueous phase gel permeation chromatography (GPC) analysis using known polymer standards appropriate for the polymer compositions involved; the polymers are subjected to hydrolysis (to the acid form) prior for determination of the backbone polymer molecular weight. Solution polymers having weight average molecular weights less than 100,000 are usefully employed as hair fixatives and applied in the form aerosols.

Polymers usefully employed according to the invention can be prepared by conventional solution polymerization. According to one embodiment of the invention, the polymers are prepared as solution polymers by a solution polymerization process, including those processes disclosed and described in U.S. Pat. Nos. 4,401,650; 4,578,267; 4,859,458; and 4,973,409. According to a separate embodiment, the polymers are prepared by optimizing the solution polymerization conditions, including situations where the polymerization kinetics are not favorable and when acid-containing monomers are used in combination with 2-acrylamido-2-methyl-1-propanesulfonic acid and salts thereof.

According to a separate embodiment, it is contemplated emulsion polymers can be prepared according to polymerization processes including those disclosed in U.S. Pat. Nos. 4,427,836; 4,469,825; 4,594,363; 4,677,003; 4,920,160; and 4,970,241 and are also prepared, for example, by polymerization techniques disclosed in European Patent Applications EP 0 267 726; EP 0 331 421; EP 0 915 108 and U.S. Pat. Nos. 4,910,229; 5,157,084; 5,663,213 and 6,384,104.

The polymers of the present invention include, as polymerized units, from 0.1 to 30%, including from 0.1 to 5% and from 5.1 to 30%, of one or more ethylenically unsaturated acid-containing monomers including monoethylenically unsaturated ($C_3$–$C_6$)carboxylic acid monomers. Suitable monoethylenically unsaturated ($C_3$–$C_6$)carboxylic acid monomers include monoethylenically unsaturated monocarboxylic acids and monoethylenically unsaturated dicarboxylic acid monomers. For example, monoethylenically unsaturated monocarboxylic acids include acrylic acid (AA), methacrylic acid (MAA), α-ethacrylic acid, β,β-dimethylacrylic acid, vinylacetic acid, allylacetic acid, ethylidineacetic acid, propylidineacetic acid, crotonic acid, and alkali and metal salts thereof. Suitable monoethylenically unsaturated dicarboxylic acid monomers include, for example, maleic acid, maleic anhydride, fumaric acid, itaconic acid, citraconic acid, mesaconic acid, methylenemalonic acid, and alkali and metal salts thereof. According to one embodiment, the monoethylenically unsaturated ($C_3$–$C_6$)carboxylic acid monomers are selected from one or more of acrylic acid and methacrylic acid. Other suitable ethylenically unsaturated acid-containing monomers include 2-methyl-2-propene-1-sulfonic acid, styrene sulfonic acid, vinyl-sulfonic acid, allylsulfonic acid, methallylsulfonic acid, allyloxybenzenesulfonic acid, methallyloxybenzenesulfonic acid, vinyl phosphonic acid and styrene phosphonic acid.

Polymers of the present invention include, as polymerized units, from 50 to 89.9%, including from 60 to 75%, of one or more copolymerizable ethylenically unsaturated monomers. Suitable copolymerizable monomers include, for example, butadiene, acrylonitrile, ethylene, di-isobutylethylene, 2-ethylhexyl acrylate, butyl acrylate, butyl methacrylate, 2-hydroxyethyl acrylate, 2-hydroxybutyl methacrylate; styrene, vinyltoluene, t-butylstyrene, isopropylstyrene, and p-chlorostyrene; vinyl acetate, vinyl butyrate, vinyl caprolate; acrylonitrile, methacrylonitrile, butadiene, isoprene, vinyl chloride, vinylidene chloride, N-vinylpyrolidone, hydroxyalkyl (meth)acrylates, ($C_1$–$C_{20}$)alkyl (meth)acrylates, poly(alkyleneoxide) di(meth)-acrylates, amides of ethylenically unsaturated ($C_3$–$C_6$)carboxylic acids, amides of ethylenically unsaturated ($C_3$–$C_6$)carboxylic acids that are substituted at the nitrogen by one or two ($C_1$–$C_4$)alkyl groups, acrylamide, methacrylamide, N-methylol (meth) acrylamide, quaternary ammonium salts of acrylamide, (3-acrylamidopropyl)trimethylammonium chloride, (3-methacrylamidopropyl)-trimethylammonium chloride, quaternary ammonium salts of (meth)acrylate esters (such as 2-(N,N,N-trimethylammonium)ethyl (meth)acrylate), 2-(dimethylamino)ethyl (meth)acrylate, N,N-dimethyl-N-methylacryloxyethyl-N-(3-sulfopropyl)-ammonium betaine, N,N-dimethylaminoethyl(meth)acrylate (DMAEMA), MAPTAC, APTAC, TBAM, TBAEMA, DMADMAM, N,N-dimethylamino-N-dimethyl(meth)acrylamide (DMADMAM), and N,N-dimethyl-N-acrylamidopropyl-N-(3-sulfopropyl)-ammonium betaine.

Polymers of the present invention include, as polymerized units, from 10 to 40% of 2-acrylamido-2-methyl-1-propanesulfonic acid and salts thereof. Additional suitable copolymerizable monomers include, for example, 2-acrylamido-2-methyl-1-propanesulfonic acid and salts thereof, 2-methacryl-amido-2-methyl-1-propanesulfonic acid and salts thereof, 3-methacrylamido-2-hydroxypropane-sulfonic acid, 2-hydroxy-3-(2-propenyloxy)propane-sulfonic acid, 3-sulfopropyl acrylate, 3-sulfopropyl methacrylate, sulfomethyl acrylamide, sulfomethyl methacrylamide and their respective metal salts.

Other monomers usefully employed in the solution polymers of the invention include non-ionic surfactant monomers incorporating long chain alkyl hydrophobic groups in the polymer, for example, such as ($C_8$–$C_{20}$)alkyl (meth) acrylate monomers (for example lauryl methacrylate) and ($C_8$–$C_{20}$)alkoxy(meth)acrylate poly(alkyleneglycol) monomers, one or more non-ionic vinyl surfactant monomers, selected from the group consisting of an acrylic or methacrylic acid ester of a $C_{12}$–$C_{24}$ alkyl monoether of a polyalkylene glycol having at least 2 oxyalkylene units therein, including those having at least 6 to 70 oxyalkylene units. Also included are the acrylate and methacrylate surfactant esters selected from the group consisting of: alkyl phenoxy poly(ethyleneoxy)ethyl acrylates and methacrylates; alkoxy poly(ethyleneoxy)ethyl acrylates and methacrylates; wherein ethyleneoxy unit is about 6–70. Such monomers may be defined by the general formula $H_2C=C(R)-C(O)-O(CH_2CH_2O)_nR'$ wherein R is H or $CH_3$, the latter being preferred, n is at least 2, and preferably has an average value of at least 6, up to 40 to 60 and even up to 70 to 100 and R' is a hydrophobic group, for example, an alkyl group or an alkyl phenyl group having 12 to 24 carbon atoms or having an average of 12 to 24 or more carbon atoms. Other suitable monomers include vinyl surfactant monomers that are acid esters of certain nonionic surfactant alcohols. Such surfactant esters are known in the art. For example, Junas et al. U.S. Pat. No. 3,652,497 describe the use of alkylphenoxypoly(ethyleneoxy)ethyl acrylates in preparing several other polymeric surfactant thickeners. Dickstein U.S. Pat. No. 4,075,411 describes several processes for preparing such vinyl surfactant esters including the acid catalyzed condensation of commercially available nonionic polyoxyalkylene surfactant alcohols such as alkylphenoxypoly(ethyleneoxy)ethyl alcohol and block-polymeric glycols with acrylic, methacrylic, crotonic, maleic, fumaric, itaconic or aconitic acid. Alternate esterification methods including alcoholysis and transesterification are also described. Other suitable vinyl surfactant esters can be prepared from monoethers of mixed or heteropolymeric ethyleneoxypropyleneoxy-butyleneoxy polyglycols such as described in Patton U.S. Pat. No. 2,786,080. Additional surfactant alcohols which can be esterified for use herein are given in "McCutcheon's Detergents and Emulsifiers" 1973, North American Edition, Allured Publishing Corp., Ridgewood, N.J. 07450.

Optionally, the solution polymers include a small amount (0.01 to 5% by weight) of at least one polyethylenically unsaturated monomer, to function as a cross-linking agent and to provide a polymer having a network structure. One or more polyethylenically unsaturated monomers may be combined with the monomers during the polymerization process or may be added after the polymerization of monomers. Suitable examples include allyl methacrylate (ALMA), ethylene glycol dimethacrylate (EGDMA), butylene glycol dimethacrylate (BGDMA), diallyl phthalate (DAP), methylenebisacrylamide, pentaerythritol di-, tri- and tetra-acrylates, divinyl benzene, polyethylene glycol diacrylates, bisphenol A diacrylates and combinations thereof. Other suitable cross-linking monomers include glycidyl methacrylate GMA, N-methylol acrylamide MOA and 2-(acetoacetoxy)ethyl methacrylate AAEM. Low levels of the polyethylenically unsaturated monomers are preferred, since levels greater than about 5% by weight tend to over cross-link the polymer or provide a polymer network structure such that their effectiveness in the invention markedly decreases.

According to one embodiment of the invention, the polymer is a copolymer composition comprising, as polymerized monomer units: (a) 50 to 89.9 weight percent of one or more ethylenically unsaturated monomers selected from acrylonitrile, ethylene, vinyl acetate, hydroxyalkyl (meth)acrylates, ($C_1$–$C_{20}$)alkyl (meth)acrylates, poly(alkyleneoxide) di(meth)-acrylates, amides of ethylenically unsaturated ($C_3$–$C_6$)carboxylic acids, amides of ethylenically unsaturated ($C_3$–$C_6$)carboxylic acids that are substituted at the nitrogen by one or two ($C_1$–$C_4$)alkyl groups, acrylamide, methacrylamide, N-methylol (meth)acrylamide, quaternary ammonium salts of acrylamide, (3-acrylamidopropyl)trimethylammonium chloride, (3-methacrylamidopropyl)-trimethylammonium chloride, quaternary ammonium salts of (meth)acrylate esters (such as 2-(N,N,N-trimethylammonium)ethyl (meth)acrylate), 2-(dimethylamino)ethyl (meth)acrylate, N,N-dimethyl-N-methylacryloxyethyl-N-(3-sulfopropyl)-ammonium betaine N,N-dimethylaminoethyl(meth)acrylate (DMAEMA), N,N-dimethylamino-N-dimethyl (meth)acrylamide (DMADMAM), and N, N-dimethyl-N-acrylamidopropyl-N-(3-sulfopropyl)-ammonium betaine and N,N-dimethyl-N-acrylamidopropyl-N-(3-sulfopropyl)-ammonium betaine; and (b) 10 to 40 weight percent of a monomer selected from 2-acrylamido-2-methyl-1-propanesulfonic acid and salts thereof, 2-methacryl-amido-2-methyl-1-propanesulfonic acid and salts thereof, 3-methacrylamido-2-hydroxypropane-sulfonic acid and salts thereof, allylsulfonic acid, methallylsulfonic acid, allyloxybenzenesulfonic acid, methallyloxybenzenesulfonic acid, 2-hydroxy-3-(2-propenyloxy)propane-sulfonic acid, 2-methyl-2-propene-1-sulfonic acid, styrene sulfonic acid, vinylsulfonic acid, 3-sulfopropyl acrylate, 3-sulfopropyl methacrylate, sulfomethyl acrylamide and sulfomethyl methacrylamide and 2-acrylamido-2-methyl-1-propanesulfonic acid and their respective salts; and incorporating in the copolymer between 0.1 to 5 weight percent of one or more acid containing ethylenically unsaturated monomers selected from one or more monoethylenically unsaturated ($C_3$–$C_6$)carboxylic acid monomers.

According to a separate embodiment of the invention, the polymer is a terpolymer composition comprising, as polymerized monomer units: (a) 60 to 75 weight percent of one or more ethylenically monomers selected from acrylonitrile, acrylamide, methacrylamide, N-methylol (meth)acrylamide, and quaternary ammonium salts of acrylamide; and (b) 20 to 30 weight percent of a monomer selected from 2-acrylamido-2-methyl-1-propanesulfonic acid and salts thereof, 2-methacryl-amido-2-methyl-1-propanesulfonic acid and salts thereof, 3-methacrylamido-2-hydroxypropane-sulfonic acid, allylsulfonic acid, methallylsulfonic acid, allyloxybenzenesulfonic acid, methallyloxybenzenesulfonic acid, 2-hydroxy-3-(2-propenyloxy)propane-sulfonic acid, 2-methyl-2-propene-1-sulfonic acid, styrene sulfonic acid, vinylsulfonic acid, 3-sulfopropyl acrylate, 3-sulfopropyl methacrylate, sulfomethyl acrylamide and sulfomethyl methacrylamide and 2-acrylamido-2-methyl-1-propanesulfonic acid and their respective salts; and (c) 2.5 to 15 weight percent of one or more acid containing ethylenically unsaturated monomers.

The polymers of the present invention have numerous advantages over polymers described in U.S. Pat. Nos. 6,569,413; 4,859,458; 4,578,267; and 4,401,650. All prior art publications describe AM/AMPS™ (AMPS™ is available from Lubrizol Corp.) copolymers neutralized with basic compounds, including base addition salts and ethoxylated fatty amines. Polymers of the invention differ significantly as compared with prior art copolymers in terms of their molecular weight distributions, polymer morphology, polymer properties and the process by which they are prepared. Polymers prepared according to and described in the latter three publications are good hair conditioners, but are poor hair fixatives. Polymers prepared by the invention are different than polymers prepared according to and described in U.S. Pat. No. 6,569,413. The compatibility of polymers of the invention in thickeners including polycarboxylic acids and carbomers such as Carbopol™ is better than comparable anionic copolymers, such as AM/AMPS™ and MAA/AMPS™ copolymers. The present invention provides multifunctional solution polymers that have utility for modifying hair, said polymers having an excellent balance of moisture (water) resistance versus water sensitivity, polymers having good color stability, good water stabilities, polymers that are non-flaking after application, and polymers that are compatible with thickeners including polyacrylic acids, paolycarboxylic acids and carbomers such as Carbopol™, providing clear, non-hazy hair formulations having stable formulation viscosities over time. Moreover, the formulations provide a smooth coating on hair, provide better adhesion to hair follicles and skin surfaces, and improve the sheen and glossiness of hair treated with the invented polymers. Inventors discovered that the formulation compatibility, clarity and viscosity stability problems associated with anionic emulsion polymers of the prior art are solved utilizing critical amounts of one or more acid-containing monomers in the polymer. The polymers of the invention are used to prepare hair formulations that are clear, non-hazy hair formulations having stable viscosities over time and are compatible with formulation additives including neutralizers, surfactants and thickeners such as polycarboxylic acids and carbomers including Carbopol™ for example. Inventors discovered that the compatibility problem with certain rheology modifiers and the viscosity stability problem, both associated with anionic solution polymers known from the prior art and described above, is unexpectedly solved by successfully including small amounts of one or more acid monomers in solution polymers of the present invention.

Solution polymers of the present invention are different as compared to the anionic solution AMPS™ homopolymers and copolymers AM/AMPS™ and MAA/AMPS™. The AMPS™ monomer and salts thereof is critical for hair conditioning, but alone does not achieve the required balance of conditioning effect versus hair modification effect. Moreover, AM/AMPS™ and MAA/AMPS™ solution copolymers lose clarity when formulated in hair treatments (e.g including hair fixatives, hair conditioners) and have poor compatibility with certain thickeners including polycarboxylic acids and carbomers, resulting in lowered and/or unstable formulation viscosities. The polymers also have undesirable humidity resistance, undesirable hair modification properties including modifying hair texture to provide the user a raspy rather than silky feeling as to hair texture and polymer flaking issues after deposition on hair. Addition of small amounts of one or more acid-containing monomers to the invented solution polymers unexpectedly improves the clarity of such polymers in formulations. Moreover, addition of small amounts of acid-containing monomers to certain copolymers known in the art also unexpectedly improves the clarity of such polymers in formulations. The solution polymers of the present invention have no such limitations and achieve the necessary balances of properties and effects when applied to mammalian skin and hair. Acid-containing ethylenically unsaturated monomers (acem) do not react well with AMPS™, and typically result in solution polymers having high levels of residual monomer after polymerization. However it was discovered that, when small amounts of such monomers are added to AM/AMPS copolymers, an unexpected improved clarity and stable viscosity is observed. The solution polymers of the invention, AMPS™/acem/AM and AMPS™/acem, further provide improved polymer clarity and stable polymer viscosities as compared to the anionic solution copolymers AM/AMPS™ and MAA/AMPS™ and AMPS™ homopolymer. Moreover, the resulting polymers of the present invention have different and unique polymer properties as compared to the anionic solution copolymers AM/AMPS™ and MAA/AMPS™. The inventors also discovered that AM copolymers and copolymers incorporating AM are markedly unique as compared with respective copolymers incorporating AA and MAA with AMPS™ monomers. AM has a better initiation profile, better polymerization kinetics and the polymerization process provides polymers with comparatively lower residual monomer levels. The process of preparing solution polymers of the invention provides a significant improvement in terms of cycle time, safety, consistency of operation, quality control, and polymer performance as compared to solution polymers known in the prior art.

Accordingly, the invention provides a process for preparing a polymer composition comprising the step of: (a) preparing a copolymer comprising, as polymerized monomer units, (i) 50 to 89.9 weight percent of one or more ethylenically unsaturated monomers and (ii) 10 to 40 weight percent of 2-acrylamido-2-methyl-1-propanesulfonic acid and salts thereof; by varying the feeds of monomers (i) and (ii) with respect to time and each monomer prior to neutralizing the polymer with a base.

The process is also referred to as a staggered feed gradual addition. In the case of a copolymer made from monomers A and B, the process comprises starting a monomer feed X minutes after monomer A feed and stooping the feed of monomer B, respectively X minutes before the feed of monomer A is stopped. The process of the invention greatly increases copolymer composition polydispersity. As time (X) increases, increasing amounts of homopolymer A are formed in the early and late stages of the process and a copolymer enriched in monomer B is formed during the middle stages of the polymerization process. The process is easily extended to include more than two monomers which can be staggered, staged or pulsed in at any time X in the polymerization process to continuously alter the resulting distribution of polymer compositions. An alternative process is to continuously change the composition of the monomer feed streams through out the polymerization and is referred to as a power feed. Polymer composition polydispersity greatly affects polymer structure, monomer connectivity sequence, weight average molecular weight (Mw), solution viscosity, rheology profile and polymer performance. All listed aspects and variants thereof can be altered using the process of the invention.

According to a separate embodiment of the present invention, the solution polymers are prepared by conventional solution polymerization techniques known in the art. For example, these polymers can be prepared by polymerization of monomers dissolved in an aqueous solvent. Both batch and continuous processes can be used. Using the gradual addition process of the invention, acrylamide derivatives are combined with anionic, cationic and non-ionic monomers to prepare a wide range of solution polymers.

The invention also provides a process for preparing a multi-functional polymer composition comprising the step of: (a) preparing a polymer comprising, as polymerized monomer units (i) 50 to 89 weight percent of one or more ethylenically unsaturated monomers, (ii) 10 to 40 weight percent of 2-acrylamido-2-methyl-1-propanesulfonic acid and salts thereof and (iii) 1 to 30 weight percent of one or more acid-containing ethylenically unsaturated monomers; by a hybrid feed that further comprises combining gradual addition and shot addition of monomers used to prepare the polymer.

Among batch processes for preparing the polymers, the hybrid feed is an unexpectedly effective process that combines both conventional single/multiple shot and gradual addition processes also referred to as a hybrid gradual addition/shot addition process. The process has a profound impact on polymer weight average molecular weight, structure and properties that is not observed in conventional addition processes. The hybrid feed process significantly increases Mw without a concomitant impact or change on solution viscosity of the resulting polymer. The hybrid feed process of the invention further provides a significant improvement in terms of cycle time, safety, consistency of operation, quality control, and polymer performance.

Optionally, the polymers of the present invention may also be made using known techniques, for example, solution (aqueous or solvent), emulsion, solvent-exchange (solution polymerization followed by phase inversion) or suspension polymerization; the polymerizations can be conducted as co-feed, heel, semi-continuous or continuous processes. The polymers may be random or block polymers depending upon the specific method used to conduct the polymerization. The polymers may be used in solution form, for example as aqueous solutions, or they may be isolated as solid materials, for example by drying, including for example spray drying, and used in the form of granules or particulates.

Conventional means for initiating the polymerization of ethylenically unsaturated monomers, including both thermal and redox initiation systems, is used. Initiators useful for these polymerizations are any of the well known freeradical-producing compounds such as peroxy, hydroperoxy and azo initiators. The polymerization of monomers is performed in a suitable solvent and in the presence of an initiator. Suitable solvents include for example water, dioxane, ketones such as 4-methylbutan-2-one, aromatic hydrocarbons such as toluene, xylene and xylene isomers, alcohols such as methanol, isopropanol and ethanol and ethers such as dioxane. Suitable reaction initiators include for example azo(bis)isobutyronitrile (AIBN), organic peroxides such as benzoyl peroxide, di-t-butyl peroxide, hydroperoxides such as t-butyl hydroperoxide and t-amyl hydroperoxide, hydrogen peroxide, sodium perborate, alkali metal persulfates and ammonium persulfate. The initiator concentration is normally between 0.01 and 6% by weight based on the total weight of the monomers, including from 0.1 to 4%. Chain transfer agents may also be added to the polymerization reaction to control the molecular weight of the polymer. Suitable chain transfer agents include alkyl mercaptans such as lauryl (dodecyl) mercaptan, carbon tetrachloride, bromoform, bromotrichloromethane, long chain alkyl mercaptans and thioesters such as n-dodecyl mercaptan, t-dodecyl mercaptan, octyl mercaptan, tetradecyl mercaptan, hexadecyl mercaptan, butyl thioglycolate, isooctyl thioglycolate, and dodecyl thioglycolate; bisulfites, phosphorous acid and salts thereof; hypophosphite salts such as sodium hypophosphite; and metal salts of Fe and Cu. The chain transfer agents are used in amounts up to 10 parts per 100 parts of polymerizable monomers. The concentration of chain transfer agent used is from 0 to about 1.0% by weight.

Water-soluble redox initiators are also used. Redox initiators include, for example, sodium bisulfite, sodium sulfite, hypophosphites, phosphites, isoascorbic acid, sodium formaldehyde-sulfoxylate and hydroxylamines, used in conjunction with suitable oxidizing agents, such as the thermal free-radical initiators noted above. The redox initiators are typically used in amounts from 0.05 to 10%, preferably from 0.5 to 5%, based on the weight of total monomer. Combinations of initiators can also be used.

Suitable oxidants of the redox initiator system include water-soluble oxidizing compounds such as, for example, hydrogen peroxide, peroxy acid salts, peroxodisulfuric acid and its salts, peroxy ester salts, ammonium and alkali metal peroxide salts, perborate salts and persulfate salts. Suitable oxidants of a redox initiator system also include water-insoluble oxidizing compounds such as, for example, dibenzoyl peroxide, t-butyl peroxide, lauryl peroxide, 2,2'-azo bis(isobutyronitrile) (AIBN), alkyl hydroperoxides such as tert-butyl hydroperoxide, tert-amyl hydroperoxide, pinene hydroperoxide and cumyl hydroperoxide, t-butyl peroxyneodecanoate, and t-butyl peroxypivalate. Compounds which donate oxygen with free radical formation and are not peroxides, such as alkali metal chlorates and perchlorates, transition metal oxide compounds such as potassium permanganate, managanese dioxide and lead oxide and organic compounds such as iodobenzene, may be usefully employed in accordance with the invention as oxidants. The term "water-insoluble" oxidants means oxidizing compounds having a water solubility of less than 20% by weight in water at 25° C. Typical levels of oxidant range from 0.01% to 3.0%, including from 0.02% to 1.0% and from 0.05% to 0.5% by weight, based on the weight of the monomer used.

Suitable reductants of the redox initiator system include reducing compounds such as, for example, sulfur compounds with a low oxidation state such as sulfites, hydrogen sulfites, alkali metal bisulfites, ketone adducts of bisulfites such as acetone bisulfite, alkali metal disulfites, metabisulfites and its salts, thiosulfates, formaldehyde sulfoxylates and its salts, reducing nitrogen compounds such as hydroxylamine, hydroxylamine hydrosulfate and hydroxylammonium salts, polyamines and reducing sugars such as sorbose, fructose, glucose, lactose and derivatives thereof, enediols such as ascorbic acid and isoascorbic acid, sulfinic acids, hydroxy alkyl sulfinic acids such as hydroxy methyl sulfinic acid and 2-hydroxy-2-sulfinacetic acid and its salts, formadinesulfinic acid and its salts, alkyl sulfinic acids such propyl sulfinic acid and isopropyl sulfinic acid, aryl sulfinic acids such as phenyl sulfinic acid. The term "salts" includes for example sodium, potassium, ammonium and zinc ions Typical levels of reductant range from 0.01% to 3.0%, including from 0.01% to 0.5% and from 0.025% to 0.25% by weight, based on the weight of the monomer used.

The metal promoter complex of the redox initiator system includes a water-soluble catalytic metal compound in the form of a salt and a chelating ligand. Suitable metal compounds include metal salts such as, for example iron(II, III) salts such as iron sulfate, iron nitrate, iron acetate and iron chloride, cobalt(II) salts, copper(I, II) salts, chromium (II) salts, manganese salts, nickel(II) salts, vanadium salts such as vanadium(III) chloride, vanadium(IV) sulfate and vanadium(V) chloride, molybdenum salts, rhodium salts and cerium(IV) salts. It is preferred that metal compounds are in the form of hydrated metal salts. Typical levels of catalytic metal salts used in accordance with the invention range from 0.01 ppm to 25 ppm. Mixtures of two or more catalytic metal salts may also be usefully employed in accordance with the invention.

Metal complexes that promote the redox cycle in a redox initiator system must not only be soluble, but must have suitable oxidation and reduction potentials. Generally stated, the oxidant must be able to oxidize the low oxidation state of metal promoter complex (e.g. Fe(II)->Fe(III)) and conversely, the reductant must be able to reduce the high oxidation state of the metal promoter catalyst (e.g. Fe(III)->Fe(II)). The choice of a particular oxidant and reductant usefully employed in a redox initiator system for preparing aqueous emulsion polymers from two or more ethylenically unsaturated monomers depends on the redox potentials of the metal salts. In addition, the ratio of oxidant to reductant ranges from 0.1:1.0 to 1.0:0.1, depending on the redox potential of the metal salt employed. For the efficient reduction of monomer levels in an aqueous polymer dispersion prepared from one or more ethylenically unsaturated monomers, it is preferred that the chelating ligand used in combination with the soluble metal salt is a multidentate aminocarboxylate ligand having fewer than six groups available for coordination to the metal salt.

Oxidant and reductant are typically added to the reaction mixture in separate streams or as a single shot, preferably concurrently with the monomer mixture. The reaction temperature is maintained at a temperature lower than 100° C. throughout the course of the reaction. Preferred is a reaction temperature between 30° C. and 85° C., preferably below 60° C. The monomer mixture may be added neat or as an emulsion in water. The monomer mixture may be added in one or more additions or continuously, linearly or not, over the reaction period, or combinations thereof. The type and amount of redox initiator systems may be the same or different in the various stages of the emulsion polymerization.

Optionally, an anionic emulsifier is included in the polymerization charge and one or more of the known nonionic emulsifiers may also be present. Examples of anionic emulsifiers are the alkali metal alkyl aryl sulfonates, the alkali metal alkyl sulfates and the sulfonated alkyl esters. Specific examples of these well-known emulsifiers are sodium dodecylbenzenesulfonate, sodium disecondary-butylnaphthalene sulfonate, sodium lauryl sulfate, disodium dodecyldiphenyl ether disulfonate, disodium n-octadecylsulfosuccinamate and sodium dioctylsulfosuccinate.

Polymerization processes for the preparation of polymers of the present invention generally result in good conversion of the monomers into polymer product. However, if residual monomer levels in the polymer mixture are undesirably high for a particular application, their levels can be reduced by any of several techniques. One common method for reducing the level of residual monomer in a polymer mixture is the post-polymerization addition of one or more initiators or reducing agents to assist scavenging of unreacted monomer.

Preferably, any post-polymerization additions of initiators or reducing agents are conducted at or below the polymerization temperature. The initiators and reducing agents suitable for reducing the residual monomer content are well known to those skilled in the art. Generally, any of the initiators suitable for the polymerization are also suitable for reducing the residual monomer content of the polymer mixture. The level of initiators or reducing agents added as a means for reducing the residual monomer content should be as low as possible to minimize contamination of the product. Generally, the level of initiator or reducing agent added to reduce the residual monomer content is in the range from 0.01 to 2.0 mole %, preferably from 0.5 to 1.0 mole %, based on the total amount (moles) of polymerizable monomer.

Further general and specific details on preparation of polymers of the present invention by solution polymerization followed by phase inversion may be found in *Progress in Organic Coatings*, 29, p 211 (1996) and *Progress in Organic Coatings*. 26, p 207 (1995).

The glass transition temperature ($T_g$) of polymers usefully employed in accordance with the invention are of a wide range and will vary according to the polymer morphology of a particular solution polymer composition. The glass transition temperature ("Tg") of the polymers used herein are those calculated by using the Fox equation (T. G. Fox, Bull. Am. Physics Soc., Volume 1, Issue No. 3, page 123(1956)). that is, for calculating the Tg of a copolymer of monomers M1 and M2, $$1/Tg(\text{calc.}) = w(M1)/Tg(M1) + w(M2)/Tg(M2),$$

wherein

Tg(calc.) is the glass transition temperature calculated for the copolymer w(M1) is the weight fraction of monomer M1 in the copolymer w(M2) is the weight fraction of monomer M2 in the copolymer Tg(M1) is the glass transition temperature of the homopolymer of M1

Tg(M2) is the glass transition temperature of the homopolymer of M2, all temperatures being in ° K.

The glass transition temperatures of homopolymers may be found, for example, in "Polymer Handbook", edited by J. Brandrup and E. H. Immergut, Interscience Publishers.

As used herein, the term "water soluble", as applied to monomers and polymers, indicates that both the monomer and resulting polymer has a solubility of at least 1 gram per 100 grams of water, preferably at least 10 grams per 100 grams of water and more preferably at least about 50 grams per 100 grams of water. The term "water insoluble", as applied to monomers and polymers, refers to monoethylenically unsaturated monomers and the resulting polymers which have low or very low water solubility under the conditions of polymerization, as described in U.S. Pat. No. 5,521,266. An aqueous system refers to any solution containing water.

Solution polymers of this invention are used as compositions for treating hair by incorporating them in a cosmetically acceptable medium in amounts of from 0.1 to about 10 weight percent, including from 0.5 to about 5 percent by weight, based on total polymer solids.

The polymers of the invention can be incorporated as compositions and formulations in various forms including hair spray, styling gel, styling glaze, spray foam, styling cream, styling wax, styling lotion, liquid foam and mousse. They can contain water and also any cosmetically acceptable solvent, in particular monoalcohols, such as alkanols having 1 to 8 carbon atoms, like ethanol, isopropanol, benzyl alcohol and phenylethyl alcohol, polyalcohols, such as alkylene glycols, like glycerins, ethylene glycol and propylene glycol, and glycol ethers, such as mono-, di- and tri-ethylene glycol monoalkyl ethers, for example ethylene glycol monomethyl ether, ethylene glycol monomethyl ether and diethylene glycol monomethyl ether, used singly or in a mixture. These solvents can be present in proportions of up to as much as 99.5 percent by weight, relative to the weight of the total composition.

The polymers of the invention are compatible in the one or more additives, including thickeners, rheology modifiers, other hair fixative polymers, other polymers, neutralizers, humectants, surfactants, conditioning agents, silicones, colors, dyes, fragrances, naturally occurring materials and preservatives; and can be neutralized at any stage of preparing the formulation. Suitable naturally occurring materials include soy bean oil, cellulose, modified cellulose, castor oil and linseed oil. In addition, the compositions and formulations incorporating polymers of this invention also can contain any other ingredient normally used in cosmetics, such as perfumes, dyestuffs (also referred to as coloring agents and colorants) which can serve to color the composition itself or the fibers (also referred to as follicles) of the hair, preservatives, sequestering agents, thickeners, silicones, softeners, foam synergistic agents, foam stabilizers, sun filters, peptizing agents and also anionic, non-ionic, cationic or amphoteric surface-active agents or mixtures thereof.

Hair fixative compositions and formulations comprising polymers of the invention are applied to wet or dry hair by spraying or by rubbing onto the hair manually. The treated hair is then mechanically fixed in the desired configuration using, for example, any of a variety of rollers or curlers. In the case of application to wet hair, the hair is then dried using ambient air, electric or hot air drying using, for example, a blow dryer. The hair is then combed to provide the desired hairstyle. After use, the hair is rinsed with water to remove the hair fixative.

According to a separate embodiment of the invention, hair fixative compositions and formulations incorporating the invented polymers are selected from the group consisting of gels, glazes and creams.

A hair styling gel is firm gel that thins upon application of shear such that it spreads very thin when applied to hair. Hair styling gels are typically applied by manually rubbing the gel onto wet or damp hair. The hair is then placed in the desired configuration, for example by wrapping the hair tightly around curlers or a finger and set by drying as described above. For a general treatise of hair styling and setting, see C. Zviak, The Science of Hair Care, 150–178 (1986).

Hair styling glazes are easy to spread, clear flowable gels that are particularly useful for the wet look or blow dry styling methods. Hair styling creams are easy to spread, flowable lotions.

In addition to the invented polymer and water and/or alcohol, the hair styling gel or glaze contains about 0.05 to about 15 percent by weight of a thickener. The thickener should be compatible with the anionic polymer and should not adversely affect the stability or efficacy of the hair styling gel. Representative thickeners include poly(meth) acrylic acids (available from Rohm and Haas Company, Philadelphia, Pa. under the tradename Acumer™), carbomers which refer to polyacrylic acid cross-linked with allyl ethers of pentaerythrol or allyl ethers of sucrose (available from BF Goodrich, Brecksville, Ohio under the tradename Carbopol™), sodium acrylates copolymer (available from Ciba Specialty Chemicals Corporation, High Point, N.C. under the tradename Salcare™), xanthan gums, sodium alginates, gum arabic and cellulose derivatives. It is also possible to achieve thickening by means of a mixture of polyethylene glycol stearates or distearates or by means of a mixture of a phosphoric acid ester and an amide.

Other optional ingredients are also incorporated into the hair styling gel or glaze. The identity of the optional ingredients is not limited as long as the optional ingredients do not adversely affect the aesthetics or efficacy of the hair styling gel. Such optional ingredients are well known to those skilled in the art and include emulsifiers such as anionic or nonionic surfactants; preservatives such as benzyl alcohol, methyl paraben, propyl paraben, or imidazolidinylurea; cationic conditioners such as cetyl trimethyl ammonium chloride, methyldibromoglutaronitrile (available from ONDEO Nalco, Naperville, Ill. under the tradename Merguard™), stearyl dimethyl benzyl ammonium chloride, isothiazolones such as Kathon™ and Neolone™ (available from Rohm and Haas Company, Philadelphia, Pa.), and di(partially hydrogenated tallow) dimethyl ammonium chloride; coloring agents such as any of the FD&C or D&C dyes; perfume oils; and chelating agents such as ethylenediaminetetraacetic acid.

Hair fixatives incorporating polymers of this invention may also contain conventional hair care adjuvants including plasticizers such as glycols, phthalate esters and glycerine, silicones, emollients, lubricants, and penetrating agents such as various lanolin compounds, protein hydrolysates and other protein derivatives, ethylene adducts and polyoxyethylene cholesterol.

The hair fixative incorporating polymers of the invention can also contain electrolytes, such as aluminum chlorohydrate, alkali metal salts, e.g., sodium, potassium or lithium salts, these salts preferably being halides, such as the chloride or bromide, and the sulphate, or salts with organic acids, such as the acetates or lactates, and also alkaline earth metal salts, preferably the carbonates, silicates, nitrates, acetates, gluconates, pantothenates and lactates of calcium, magnesium and strontium. Other suitable electrolytes are metal cross-linking agents including salts of magnesium, calcium and zinc. The metal salts are also suitable cross-linking agents used in preparing cross-linked solution polymers of the invention.

The hair fixatives prepared using polymers of this invention may also contain one or more additional hair fixative polymers. When present, the additional hair fixative polymers are present in a total amount of from about 0.25 to about 5 percent by weight. Representative hair fixative polymers compatible with anionic and nonionic hair fixative polymers include acrylic/acrylate copolymers, allyl stearate/vinyl acetate (VA) copolymers, AMP acrylate/diacetoneacrylamide copolymers, butyl ester of ethylene/maleic anhydride (MA) copolymers, butyl ester of PVM/MA copolymers, acrylate/C1–20 succinate/hydroxyacrylate copolymers, including Allianz™ LT-120 (available from Rohm and Haas Company, Philadelphia, Pa. and ISP, Wayne, N.J.), acrylate/hydroxyester acrylates, including Acudyne™ 180 (available from Rohm and Haas Company, Philadelphia, Pa.), isopropyl ester of PVM/MA copolymers, octylacrylamide/acrylate/butylaminoethyl methacrylate copolymers, phthalic anhydride/glycerin/glycidyl decanoate copolymers, polybutylene terephthalate PBT, polyethylacrylate, polyethylene, polyvinyl acetate, polyvinyl butyral, polyvinyl methyl ether, polyvinylprrolidinone (PVP), poly N-vinylformamide, PVP/VA copolymers, PVP/dimethylaminoethylmethacrylate copolymers, PVP/eicosene copolymers, PVP/ethyl methacrylate/methacrylic acid copolymers, PVP/hexadecene copolymers, PVP/VA/itaconic acid copolymers, sodium acrylate/vinyl alcohol copolymers, starch diethylaminoethyl ether, stearylvinyl ether/maleic anhydride copolymers, VA/crotonate copolymers, VA/crotonic acid copolymers, VA/crotonic acid/methacryloxybenzophenone-1 copolymers, VA/crotonic acid/vinyl neodecanoate copolymers, and combinations thereof.

Hair styling gels using polymers of the present invention are prepared by dissolving the invented polymers in water or a water/alcohol mixture, with heating if necessary. An aqueous solution of the viscosity enhancer and any optional ingredients are then added and the mixture is stirred to provide the gel or glaze.

When the hair fixative incorporating invented polymers is in the form of a hair spray or mousse, it additionally contains up to 50 weight percent of one or more propellants. Typical propellants include ethers, compressed gases, halogenated hydrocarbons and hydrocarbons including, dimethyl ether, carbon dioxide, nitrogen, nitrous oxide and volatile hydrocarbons, such as butane, isobutane, propane, and the like.

Polymers of the invention are easily incorporated into other useful compositions and formulations, including but not limited to, gels, setting agents, setting creams, pomade, waxing agents, oil treatments, foams, mousses, gels that can be sprayed, shine agents, conditioners left on skin and hair, conditioning agents, softeners, rinse off conditioners, shampoos, shampoos including conditioners, hair color treatments, hair bleaching treatments, agents for increasing hair volume, moisturizers, soaps, cosmetics, body washes, shaving preparations (e.g. lotions, creams, gels and glazes), sunscreens, topical skin and eye treatments.

The invented polymers are usefully employed for cosmetic purposes as film formers without requiring addition of other materials, for example, such as a hair fixative, skin barrier, or clear nail polish. The polymers can also be formulated with other ingredients known to the cosmetic industry and registered under CTFA International Cosmetic Ingredients Dictionary and Handbook. Such ingredients include emollients, humectants, other film forming polymers, propellants, solvents, pigments, dyes, buffers, organic and inorganic suspending and thickening agents, waxes, surfactants and co-surfactants, plasticizers, organic and inorganic neutralizing agent, preservatives, flavoring agents, perfumes, and active ingredients including sunscreen agents, insect repellents, vitamins, herbal extracts, antiperspirant and deodorant agents, skin or hair bleaching or coloring agents, depilating agents, anti-fungal and antimicrobial agents, anti-dandruff and anti-acne agents, astringents, and combinations thereof.

Cationic surfactants are also usefully employed as additives in compositions and formulations of the invention. Non-ionic surfactants are also usefully employed as additives in the invention. In one embodiment they are additives. Non-ionic surfactants are surfactants having no charge when dissolved or dispersed in aqueous solutions. Amphoteric or zwitterionic surfactants (such as cocamidopropyl betaine) including both acidic and basic hydrophilic groups and can also be used as additives in the present invention.

The solution polymers of the invention are processed into solids by conventional techniques including but not limited to freeze drying, evaporation, evaporation under reduced pressure, spray drying, fluidized spray drying and coagulation using cationic surfactants, polyelectrolytes, metal salts or combinations thereof. The drying/isolation technique usefully employed according to the invention will vary depending on the nature of the aqueous emulsion polymer, the surfactant(s) utilized and combinations thereof.

The invention provides a manufacturing process for preparing solution polymers that have desired rheology and polymer properties for incorporating into compositions and formulations used in treating and modifying skin and hair, including those used in personal care, cosmetic, consumer, and pharmaceutical products.

Some embodiments of the invention are described in detail in the following Examples. All ratios, parts and percentages are expressed by weight unless otherwise specified, and all reagents used are of good commercial quality unless otherwise specified. The following abbreviations are used in the Examples:

AM=Acrylamide
AMPS=2-acrylamido-2-methyl-1-propanesulfonic acid, sodium salt
MAA=Methacrylic Acid
AA=Acrylic Acid Brookfield viscosities of invented polymers and of hair compositions and hair formulations incorporating invented polymers were measured using a commercially available Brookfield viscometer. Details of the Brookfield viscosity measurements, and interpretation of Brookfield values are described by Christopher W. Macosko in "Rheology: Principles, Measurements and Applications, VCH Publishers: New York, 1994.

EXAMPLE 1

(75AM/25 AMPS™). Comparative Example 1

The 75AM/25AMPS™ copolymer was prepared according to the method described in U.S. Pat. No. 4,578,267 as a comparative example. A one liter resin kettle with overhead stirrer, $N_2$ inlet, condenser, thermocouple, heating mantle, and provision for external cooling was set up in a hood. 24.5 g of AMPS™ (0.118 m) was dissolved in 118 ml of 1N NaOH and the pH adjusted to 8, the total weight was 159.3 g. This solution was then added to the kettle along with 152.8 g of 49.4% Dow aqueous acrylamide (1.06 m) and 100 ml of $H_2O$. Then 0.038 g of $CuCl_2.2H_2O$ dissolved in 62 ml of $H_2O$ was added. Heating, stirring, and $N_2$ purging was performed. After about 40 minutes when, after reaching a temperature of 50° C., the heating mantle was removed and 0.50 g of $(NH_4)_2S_2O_8$ dissolved in 25 ml of $H_2O$ was added, the temperature fell to 46° C.–47° C. Within 5 minutes the exotherm started, the solution became thicker, and the $N_2$ flow was reduced and removed to the head space. The calculated heat of polymerization at room temperature was 22.5° C., based on a 25% aqueous acrylamide solution. External cooling was applied to maintain the temperature at or below 60° C. After completion of the exotherm, a temperature of 50° C. was maintained. A sample was removed after 2 hours for acrylamide analysis, the nitrogen turned off, and 0.63 g of $NaHSO_3$ (0.5 mole % based on acrylamide) dissolved in 25 ml of $H_2O$ was added. After stirring for an hour, vacuum was pulled for 1–3 minutes several times over about a 15 minute period to help remove excess $SO_2$. While stirring vigorously, 118 g (0.059 m) of soyabis(polyoxyethylene)15 amine was added with 75 ml of wash $H_2O$ over about 15 minutes period. After the additions, the pH was 8. Citric acid solution (25 g) was added to lower the pH to 6+/−0.5. The intrinsic viscosity of the polymer-sodium salt was 1.04 dl/g measured in 5.05 N NaCl at 29° C.

EXAMPLE 2

75AM/25 AMPS

The 75AM/25AMPS™ copolymer was prepared by modifying the method described in U.S. Pat. No. 4,578,267 by omitting the use of ethoxylated amine neutralizer. A one liter resin kettle with overhead stirrer, $N_2$ inlet, condenser, thermocouple, heating mantle, and provision for external cooling was set up in a hood. DI water (250.25 g) along with 133.9 g of AMPS-sodium salt (50.5%, from Lubrizol) was charged to the kettle. Next, 378.95 g of 50% aqueous acrylamide from Cytec followed by 0.102 g of $CuCl_2$ dissolved in 155.25 g DI water was added and the mixture was heated to 50° C. under $N_2$ with stirring. The heating mantle was removed and 1.3 g of $(NH_4)_2S_2O_8$ dissolved in 62.5 ml of $H_2O$ was added. Within 2 minutes the exotherm started, the solution became thicker, and the $N_2$ flow was reduced and removed to the head space. The exotherm peaked at 99° C. five minutes after the initiator addition. After completion of the exotherm, a temperature of 60° C. was maintained for 3 hours with constant stirring. Samples were removed every hour for acrylamide and MW analysis. Sodium bisulfite (1.53 g dissolved in 90.25 g DI water) was added. After stirring for an hour, vacuum was pulled for 1–3 minutes several times over about a 15 minute period to help remove excess $SO_2$. The reaction mixture was then cooled and packaged. It had a polymer solids content of 26.8% and pH 3.75. A viscosity of 122,000 centipoise (cps) was measured using a conventional Brookfield viscometer.

EXAMPLE 3

Modified Shot Process, 90 AM/10 AMPS

The 90AM/10AMPS™ copolymer having improved performance was prepared by a modified shot process and provided a significantly shorter cycle time. A one liter resin kettle with overhead stirrer, $N_2$ inlet, condenser, thermocouple, heating mantle, and provision for external cooling was set up in a hood. DI water (125 g) along with 25.43 g of AMPS-sodium salt (50.5%, from Lubrizol) was charged to the kettle. Next, 231.2 g of 50% aqueous acrylamide from Cytec followed by 0.051 g of $CuCl_2$ dissolved in 77.6 g DI water was added and the mixture was heated to 50° C. under $N_2$ with stirring. The heating mantle was removed and 0.65 g of $(NH_4)_2SO_2O_8$ dissolved in 31 ml of $H_2O$ was added. Within 2 minutes the exotherm started, the solution became thicker, and the $N_2$ flow was reduced and removed to the head space. The exotherm peaked at 97° C. four minutes after the initiator addition. After completion of the exotherm, a temperature of 85° C. was maintained for 30 minutes with constant stirring. A sample was removed for acrylamide and MW analysis. Sodium bisulfite (0.77 g dissolved in 45 g DI water) was added. After stirring for an hour, vacuum was pulled for 1–3 minutes several times over about a 15 minute period to help remove excess $SO_2$. The reaction mixture was then cooled and packaged. It had a polymer solids content of 27.8%. A viscosity of >200,000 centipoise (cps) was measured using a conventional Brookfield viscometer.

EXAMPLE 4

Modified Shot Process, 60 AM/40 AMPS

The 60AM/40AMPS™ copolymer having improved performance was prepared by a modified shot process and provided a significantly shorter cycle time. A one liter resin kettle with overhead stirrer, $N_2$ inlet, condenser, thermocouple, heating mantle, and provision for external cooling was set up in a hood. DI water (125 g) along with 101.7 g of AMPS-sodium salt (50.5%, from Lubrizol) was charged to the kettle. Next, 154.2 g of 50% aqueous acrylamide from Cytec followed by 0.051 g of $CuCl_2$ dissolved in 77.6 g DI water was added and the mixture was heated to 50° C. under $N_2$ with stirring. The heating mantle was removed and 0.65 g of $(NH_4)_2S_2O_8$ dissolved in 31 ml of $H_2O$ was added. Within 2 minutes the exotherm started, the solution became thicker, and the $N_2$ flow was reduced and removed to the head space. The exotherm peaked at 92° C. twenty-five minutes after the initiator addition. After completion of the exotherm, a temperature of 85° C. was maintained for 30 minutes with constant stirring. A sample was removed for acrylamide and MW analysis. Sodium bisulfite (0.77 g dissolved in 45 g DI water) was added. After stirring for an hour, vacuum was pulled for 1–3 minutes several times over about a 15 minute period to help remove excess $SO_2$. The reaction mixture was then cooled and packaged. Polymer solids level was 26.9%. A viscosity of 45,100 centipoise (cps) was measured using a conventional Brookfield viscometer.

EXAMPLE 5

Modified Shot Process, Initiation at 40° C., 80 AM/20 AMPS

The 80AM/20AMPS™ copolymer having improved performance was prepared by a modified shot process and demonstrated that initiation can occur at lower temperatures, resulting in a lower, more controlled (safer) exotherm. A one liter resin kettle with overhead stirrer, $N_2$ inlet, condenser, thermocouple, heating mantle, and provision for external cooling was set up in a hood. DI water (170 g) along with 51.4 g of AMPS-sodium salt (50.5%, from Lubrizol) was charged to the kettle. Next, 195.06 g of 50% aqueous acrylamide from Cytec followed by 0.051 g of $CuCl_2$ dissolved in 77.6 g DI water was added and the mixture was heated to 40° C. under $N_2$ with stirring. The heating mantle was removed and 0.65 g of $(NH_4)_2S_2O_8$ dissolved in 31 ml of $H_2O$ was added. Within 5 minutes the exotherm started, the solution became thicker, and the $N_2$ flow was reduced and removed to the head space. The exotherm peaked at 82° C. fifteen minutes after the initiator addition. After completion of the exotherm, a temperature of 82° C. was maintained for 60 minutes with constant stirring. Samples were periodically removed for acrylamide and MW analysis. The reaction mixture was then cooled and packaged. Polymer solids level was 25.6%. A viscosity of 167,000 centipoise (cps) was measured using a conventional Brookfield viscometer.

EXAMPLE 6

Modified Shot Process, Initiation at 40° C., 20 AM/80 AMPS

The 20AM/80AMPS™ copolymer having improved performance was prepared by a modified shot process and demonstrated that initiation can occur at lower temperatures, resulting in a lower, more controlled (safer) exotherm. A one liter resin kettle with overhead stirrer, $N_2$ inlet, condenser, thermocouple, heating mantle, and provision for external cooling was set up in a hood. DI water (125 g) along with 205.6 g of AMPS-sodium salt (50.5%, from Lubrizol) was charged to the kettle. Next, 48.76 g of 50% aqueous acrylamide from Cytec followed by 0.051 g of $CuCl_2$ dissolved in 77.6 g DI water was added and the mixture was heated to 40° C. under $N_2$ with stirring. The heating mantle was removed and 0.65 g of $(NH_4)_2SO_2O_8$ dissolved in 31 ml of $H_2O$ was added. Within 1 minute the exotherm started, the solution became thicker, and the $N_2$ flow was reduced and removed to the head space. The exotherm peaked at 65° C. five minutes after the initiator addition. After completion of the exotherm, a temperature of 65° C. was maintained for 120 minutes with constant stirring. Samples were periodically removed for acrylamide and MW analysis. The reaction mixture was then cooled and packaged. Polymer solids level was 30.0%. A viscosity of 4,900 centipoise (cps) was measured using a conventional Brookfield viscometer.

EXAMPLE 7

Modified Shot Process, Initiation at 50° C. with Low Solids, 60 AM/40 AMPS

The 60AM/40AMPS™ copolymer having improved performance was prepared by a modified shot process and demonstrated that initiation can occur at lower solids, resulting in lower, more controlled (safer) exotherm and lower viscosity, both significant scale-up and manufacturing advantages. A one liter resin kettle with overhead stirrer, $N_2$ inlet, condenser, thermocouple, heating mantle, and provision for external cooling was set up in a hood. DI water (165 g) along with 51.4 g of AMPS-sodium salt (50.5%, from Lubrizol) was charged to the kettle. Next, 72.32 g of 50% aqueous acrylamide from Cytec followed by 0.026 g of $CuCl_2$ dissolved in 77.6 g DI water was added and the mixture was heated to 50° C. under $N_2$ with stirring. The heating mantle was removed and 0.325 g of $(NH_4)_2S_2O_8$ dissolved in 31 ml of $H_2O$ was added. Within 1 minute the exotherm started, the solution became thicker, and the $N_2$ flow was reduced and removed to the head space. The exotherm peaked at 63° C. fifteen minutes after the initiator addition. After completion of the exotherm, a temperature of 63° C. was maintained for 30 minutes with constant stirring. Sodium bisulfite (0.28 g dissolved in 30 g DI water) was added. After stirring for 40 minutes at 63° C., the reaction mixture was then cooled and packaged. Polymer solids level was 14.5%. A viscosity of 1,670 centipoise (cps) was measured using a conventional Brookfield viscometer.

EXAMPLE 8

Gradual Addition Process, 80 AM/20 AMPS

The 80AM/20AMPS™ copolymer having improved performance was prepared by a gradual addition process and resulted in a marked process improvement, in terms of temperature, viscosity and weight average molecular weight control. A one liter resin kettle with overhead stirrer, $N_2$ inlet, condenser, thermocouple, heating mantle, and provision for external cooling was set up in a hood. DI water (170 g) was charged to the kettle and heated to 88° C. under $N_2$. A mixture of 51.4 g of AMPS-sodium salt (50.5%, from Lubrizol) and 193.9 g of 50% aqueous acrylamide from Cytec was metered in to the reactor over 90 minutes along with a solution of 0.65 g of $(NH_4)_2S_2O_8$ dissolved in 60 g of $H_2O$. The viscosity of the mixture gradually increased as the reaction proceeded. The mixture was diluted with 40 ml DI-water and held at 88° C. for 30 minutes. It was then cooled to room temperature and packaged. Polymer solids level was 25.5% and viscosity was measured to be 7190 cps.

EXAMPLE 9

Gradual Addition Process, 75 AM/25 AMPS

The 75AM/25AMPS copolymer having improved performance was prepared by a gradual addition process. Same as Example 8 but using 66.95 g AMPS and 179.69 g Am and 60 minute feed. 27.1% polymer solids and 13,650 cps viscosity were measured for the polymer.

EXAMPLE 10

Gradual Addition Process, 60 AM/40 AMPS

The 60AM/40AMPS™ copolymer having improved performance was prepared by a gradual addition process. Same as Example 8 but using 102.8 g AMPS and 145.5 g Am. 25.4% polymer solids and 1420 cps viscosity were measured for the polymer.

EXAMPLE 11

Gradual Addition Process, 40 AM/60 AMPS

The 40AM/60AMPS™ copolymer having improved performance was prepared by a gradual addition process. Same as Example 8 but using 154.2 g AMPS and 96.98 g Am. 26.4% polymer solids and 960 cps viscosity were measured for the polymer.

EXAMPLE 12

Gradual Addition Process, 50 AM/50 AMPS

The 50AM/50AMPS™ copolymer having improved performance was prepared by a gradual addition process. Same as Example 8 but using 128.5 g AMPS and 121.22 g Am. 25.9% polymer solids and 630 cps viscosity were measured for the polymer.

EXAMPLE 13

Gradual Addition Process, 20 AM/80 AMPS

The 20AM/80AMPS™ copolymer having improved performance was prepared by a gradual addition process. Same as Example 8 but using 205.6 g AMPS and 48.49 g Am. 25.7% polymer solids and 240 cps viscosity were measured for the polymer.

EXAMPLE 14

Gradual Addition Process, 60 AM/40 AMPS-Acid

The 60AM/40AMPS™ copolymer having improved performance was prepared by a gradual addition process and demonstrates utility with solid grade (free acid form) of AMPS™ monomer. A one liter resin kettle with overhead stirrer, $N_2$ inlet, condenser, thermocouple, heating mantle, and provision for external cooling was set up in a hood. DI water (120 g) was charged to the kettle and heated to 88° C. under $N_2$. A mixture of 51.4 g of AMPS™ monomer (Lubrizol) dissolved 60 ml DI-water and 145.5 g of 53% aqueous acrylamide from Cytec was metered in to the reactor over 90 minutes along with a solution of 0.65 g of $(NH_4)_2S_2O_8$ dissolved in 100 g of DI-$H_2O$. The viscosity of the mixture gradually increased as the reaction proceeded. Following addition of the reagents, the mixture was held at 88° C. for 30 minutes and then a solution of 0.56 g sodium bisulfite dissolved in 40 g DI-$H_2O$ was added. The temperature was maintained at 88° C. for another 30 minutes, then the mixture was cooled to room temperature and packaged. Polymer solids level 25.3%, pH 2.4 and a viscosity of 9320 cps were measured for the polymer.

(Gradual Addition Process, 60 AM/40 AA). Comparative Example 2

The 60AM/40AA copolymer having improved performance was prepared by a gradual addition process. The process exhibited poor polymerization kinetics, the polymer had high amounts of residual monomers and low formulation viscosity. Same as Example 10 but with AA replacing AM.

(Gradual Addition Process, 60 MAA/40 AMPS). Comparative Example 3

The 60AM/40MAA copolymer having improved performance was prepared by a gradual addition process. A one liter resin kettle with overhead stirrer, $N_2$ inlet, condenser, thermocouple, heating mantle, and provision for external cooling was set up in a hood. DI water (145 g) was charged to the kettle and heated to 88° C. under $N_2$. A mixture of 75.4 g of AMPS-sodium salt (50.5%, from Lubrizol), 60.0 g of MAA (Rohm and Haas) and 20 g DI-$H_2O$ was metered in to the reactor over 90 minutes along with a solution of 0.50 g of $(NH_4)_2S_2O_8$ dissolved in 20 g of $H_2O$ which was metered in over 97 minutes. The viscosity of the mixture gradually increased as the reaction proceeded. Following addition of the reagents, the mixture was held at 88° C. for 5 minutes, then a solution of 0.25 g sodium bisulfite dissolved in 20 g DI-$H_2O$ was metered in over 15 minutes. The mixture was cooled to room temperature and packaged.

EXAMPLE 15

Gradual Addition Process, 60 AM/30 AMPS/10 AA

The 60AM/10AA/30AMPS™ terpolymer having improved performance was prepared by a gradual addition process. A one liter resin kettle with overhead stirrer, $N_2$ inlet, condenser, thermocouple, heating mantle, and provision for external cooling was set up in a hood. DI water (170 g) was charged to the kettle and heated to 88° C. under $N_2$. A mixture of 77.1 g of AMPS™-sodium salt (50.5%, from Lubrizol), 144.68 g of 53.3% aqueous acrylamide from Cytec, 12.85 g AA (Rohm and Haas) and 30 g DI-$H_2$O was metered in to the reactor over 90 minutes along with a solution of 0.65 g of $(NH_4)_2S_2O_8$ dissolved in 60 g of $H_2O$. The viscosity of the mixture gradually increased as the reaction proceeded. Following addition of the reagents, the mixture was held at 88° C. for 30 minutes and then a solution of 0.56 g sodium bisulfite dissolved in 20 g DI-$H_2$O was added. The temperature was maintained at 88° C. for another 30 minutes, then the mixture was cooled to room temperature and packaged. Polymer solids 27.2%, pH 4.4 and viscosity of 1240 cps were measured for the polymer.

EXAMPLE 16

Gradual Addition Process, 60 AM/30 AMPS/10 MAA

The 60AM/10MAA/30AMPS™ terpolymer having improved performance was prepared by a gradual addition process. Same as Example 15 except AA is replaced with MAA. Polymer solids level of 24.3%, pH 4.99 and viscosity of 840 cps were measured for the polymer.

EXAMPLE 17

Gradual Addition Process, 75 AM/15 AMPS/10 MAA

The 75AM/10MAA/15AMPS terpolymer having improved performance was prepared by a gradual addition process. Same as Example 15 but using 38.55 AMPS, 180.81 AM and 12.85 MAA. It had a polymer solids level of 26.9%, pH 4.69 and a viscosity of 3430 cPs was measured for the polymer.

EXAMPLE 18

Gradual Addition Process, 60 AM/20 AMPS/20 MAA

The 60AM/20MAA/20AMPS™ terpolymer having improved performance was prepared by a gradual addition process. Same as Example 15 but using 51.4 AMPS, 145.47 AM and 25.7 MAA and 15 g DI water rinse. Polymer solids 28.8%, pH 4.94 and a viscosity of 5200 cps were measured for the polymer.

EXAMPLE 19

Gradual Addition Process, 60 AM/10 AMPS/30 MAA

The 60AM/30MAA/10AMPS™ terpolymer having improved performance was prepared by a gradual addition process. Same as Example 15 but using 25.7 AMPS, 145.47 AM and 38.35 MAA. Polymer solids level of 28.4%, pH 4.94 and a viscosity of 3700 cps were measured for the polymer.

EXAMPLE 20

Gradual Addition Process, 30 AM/60 AMPS/10 MAA

The 30AM/10MAA/60AMPS™ terpolymer having improved performance was prepared by a gradual addition process. A one liter resin kettle with overhead stirrer, $N_2$ inlet, condenser, thermocouple, heating mantle, and provision for external cooling was set up in a hood. DI water (170 g) was charged to the kettle and heated to 88° C. under $N_2$. A mixture of 154.2 g of AMPS™-sodium salt (50.5%, from Lubrizol), 72.73 g of 53.3% aqueous acrylamide from Cytec, 12.85 g MAA (Rohm and Haas) and 15 g DI-$H_2$O was metered in to the reactor over 90 minutes along with a solution of 0.65 g of $(NH_4)_2S_2O_8$ dissolved in 60 g of $H_2O$ which was metered in over 95 minutes. The viscosity of the mixture gradually increased as the reaction proceeded. Following addition of the reagents, the mixture was held at 88° C. for 10 minutes, then cooled to 60° C. and a solution of 0.33 g sodium bisulfite dissolved in 20 g DI-$H_2$O was added. The temperature was maintained at 60° C. for another 30 minutes, then the mixture was cooled to room temperature and packaged. It had a polymer solids level of 27.1%.

EXAMPLE 21

Gradual Addition Process, 70 AM/25 AMPS/5 MAA

The 70AM/5MAA/25AMPS™ terpolymer having improved performance was prepared by a gradual addition process. Same as Example 20 but using 64.25 AMPS, 169.71 g AM, and 6.43 g MAA. It had a polymer solids level of 26.7%, pH 4.53 and a viscosity of 1540 cps was measured for the polymer.

EXAMPLE 22

Gradual Addition Process, 75 AM/20 AMPS/5 MAA

The 75AM/5MAA/20AMPS™ terpolymer having improved performance was prepared by a gradual addition process. Same as Example 20 but using 51.4 AMPS, 181.84 g AM, and 6.43 g MAA. Polymer solids of 26.6%, pH 4.58 and a viscosity of 2150 cps were measured for the polymer.

EXAMPLE 23

Gradual Addition Process, 65 AM/32.5 AMPS/2.5 MAA

The 65AM/2.5MAA/32.5AMPS™ terpolymer having improved performance was prepared by a gradual addition process. Same as Example 20 but using 83.52 AMPS, 157.59 g AM, and 3.21 g MAA. Polymer solids of 26.5%, pH 4.56 and a viscosity of 1360 cps were measured for the polymer.

EXAMPLE 24

Gradual Addition Process, 60 AM/37.5 AMPS/2.5 MAA

The 60AM/2.5MAA/37.5AMPS™ terpolymer having improved performance was prepared by a gradual addition process. Same as Example 20 but using 96.37 AMPS, 145.47 g AM, and 3.21 g MAA. Polymer solids level of 26.9%, pH 4.63 and a viscosity of 1300 cps were measured for the polymer.

EXAMPLE 25

Gradual Addition Process, 65 AM/30 AMPS/5 MAA

The 65AM/5MAA/30AMPS™ terpolymer having improved performance was prepared by a gradual addition process. A one liter resin kettle with overhead stirrer, $N_2$ inlet, condenser, thermocouple, heating mantle, and provision for external cooling was set up in a hood. DI water (170 g) was charged to the kettle and heated to 88° C. under $N_2$. A mixture of 77.1 g of AMPS™-sodium salt (50.5%, from Lubrizol), 157.59 g of 53.3% aqueous acrylamide from Cytec, 6.43 g MAA (Rohm and Haas) and 15 g DI-$H_2$O was metered in to the reactor over 90 minutes along with a solution of 0.65 g of $(NH_4)_2S_2O_8$ dissolved in 60 g of $H_2$O which was metered in over 95 minutes. The viscosity of the mixture gradually increased as the reaction proceeded. Following addition of the reagents, the mixture was held at 88° C. for 10 minutes, then cooled to 60° C. and a solution of 0.33 g sodium bisulfite dissolved in 20 g DI-$H_2$O and 1.28g of 0.15% FeSO4.$H_2$O was added over 15 minutes. The temperature was maintained at 60° C. for another 30 minutes, then the mixture was cooled to room temperature and packaged. Polymer solids level of 26.8%, pH 4.86 and a viscosity of 1440 cps were measured for the polymer.

EXAMPLE 26

Gradual Addition Process, 65 AM/30 AMPS/5 MAA

The 65AM/5MAA/30AMPS™ terpolymer having improved performance was prepared by a gradual addition process. A one liter resin kettle with overhead stirrer, $N_2$ inlet, condenser, thermocouple, heating mantle, and provision for external cooling was set up in a hood. DI water (145 g) was charged to the kettle and heated to 88° C. under $N_2$. A mixture of 60 g of AMPS™-sodium salt (50.5%, from Lubrizol), 130 g of 53.3% aqueous acrylamide from Cytec, 5.0 g MAA (Rohm and Haas) and 20 g DI-$H_2$O was metered in to the reactor over 60 minutes along with a solution of 0.5 g of $(NH_4)_2S_2O_8$ dissolved in 20 g of $H_2$O which was metered in over 67 minutes. The viscosity of the mixture gradually increased as the reaction proceeded. Following addition of the reagents, the mixture was held at 88° C. for 5 minutes, and a solution of 1.0 g of 0.15% FeSO4.$H_2$O was added. Next, 0.25 g sodium bisulfite dissolved in 10 g DI-$H_2$O and 0.25 g $(NH_4)_2S_2O_8$ dissolved in 10 g of $H_2$O was added over 15 minutes. The mixture was cooled to room temperature and packaged. Polymer solids of 26.4%, pH 4.4 and a viscosity of 1440 cps were measured for the polymer.

EXAMPLE 27

Gradual Addition Process, 80 AM/17.5 AMPS/2.5 MAA

The 80AM/2.5MAA/17.5AMPS™ terpolymer having improved performance was prepared by a gradual addition process. Same as EXAMPLE 20 but using 47.54 AMPS, 193.97 g AM, and 3.21 g MAA. Polymer solids of 27.1%, pH 4.5 and a viscosity of 3760 cps were measured for the polymer.

EXAMPLE 28

Gradual Addition Process, 60 AM/30 Ammonium AMPS/5 MAA

The 60AM/5MAA/30NH$_4$AMPS™ terpolymer having improved performance was prepared by a gradual addition process and demonstrates utility with AMPS™-ammonium salt. A one liter resin kettle with overhead stirrer, $N_2$ inlet, condenser, thermocouple, heating mantle, and provision for external cooling was set up in a hood. DI water (145 g) was charged to the kettle and heated to 88° C. under $N_2$. A mixture of 60.0 g of AMPS™-ammonium salt (50%, from Lubrizol), 130.0 g of AM (50% aqueous solution), 5 g of MAA (Rohm and Haas) and 20 g DI-$H_2$O was metered in to the reactor over 90 minutes along with a solution of 0.50 g of $(NH_4)_2S_2O_8$ dissolved in 20 g of $H_2$O which was metered in over 97 minutes. The viscosity of the mixture gradually increased as the reaction proceeded. Following addition of the reagents, the mixture was held at 88° C. for 5 minutes, then a solution of 0.25 g sodium bisulfite dissolved in 20 g DI-$H_2$O was metered in over 15 minutes. The mixture was cooled to room temperature and packaged.

EXAMPLE 29

Gradual Addition Process, 65 AM/30 AMPS/5 MAA

The 65AM/5MAA/30AMPS™ terpolymer was prepared by a gradual addition process. A one liter resin kettle with overhead stirrer, $N_2$ inlet, condenser, thermocouple, heating mantle, and provision for external cooling was set up in a hood. DI water (145 g) was charged to the kettle and heated to 88° C. under $N_2$. A mixture of 60 g of AMPS-sodium salt (50.5%, from Lubrizol), 130 g of 53.3% aqueous acrylamide from Cytec, 5.0 g MAA (Rohm and Haas) and 20 g DI-$H_2$O was metered in to the reactor over 60 minutes along with a solution of 0.5 g of $(NH_4)_2S_2O_8$ dissolved in 20 g of $H_2$O which was metered in over 67 minutes. The viscosity of the mixture gradually increased as the reaction proceeded. Following addition of the reagents, the mixture was held at 88° C. for 5 minutes, and a solution of 1.0 g of 0.15% FeSO4.$H_2$O was added. Next, 0.25 g sodium bisulfite dissolved in 10 g DI-$H_2$O and 0.25 g $(NH_4)_2S_2O_8$ dissolved in 10 g of $H_2$O was added over 15 minutes. The mixture was cooled to room temperature and packaged. Polymer solids were 26.4%, pH 4.4 and measured viscosity was 1440 cPs.

EXAMPLE 30

Gradual Addition Process, 65 Methacrylamide/30 AMPS/5 MAA

The 65MAM/5MAA/30AMPS™ terpolymer was prepared by a gradual addition process. A one liter resin kettle with overhead stirrer, $N_2$ inlet, condenser, thermocouple, heating mantle, and provision for external cooling was set up in a hood. DI water (105 g) was charged to the kettle and heated to 88° C. under $N_2$. A mixture of 60 g of AMPS-sodium salt (51.2%, from Lubrizol), 305 g of 21.3% aqueous methacrylamide, 5.0 g MAA (Rohm and Haas) and 20 g DI-$H_2O$ was metered in to the reactor over 60 minutes along with a solution of 0.5 g of $(NH_4)_2S_2O_8$ dissolved in 20 g of $H_2O$ which was metered in over 67 minutes. The initiator was pre-fed 2 minutes prior to the monomer feed and post-fed 5 minutes after the monomer feed was completed. The viscosity of the mixture gradually increased as the reaction proceeded. Following addition of the reagents, the mixture was held at 88° C. for 5 minutes, and a solution of 1.0 g of 0.15% FeSO4.$H_2O$ was added. Next, 0.25 g sodium bisulfite dissolved in 10 g DI-$H_2O$ and 0.25 g $(NH_4)_2S_2O_8$ dissolved in 10 g of $H_2O$ was added over 15 minutes. The mixture was cooled to room temperature and packaged. Polymer solids were 20.1%, pH 4.8 and measured viscosity was 250 cPs.

EXAMPLE 31

Gradual Addition Process, 65 Isopropylacrylamide/30 AMPS/5 MAA

The terpolymer was prepared by a gradual addition process. A one liter resin kettle with overhead stirrer, $N_2$ inlet, condenser, thermocouple, heating mantle, and provision for external cooling was set up in a hood. DI water (105 g) was charged to the kettle and heated to 88° C. under $N_2$. A mixture of 60 g of AMPS-sodium salt (51.2%, from Lubrizol), 305 g of 21.3% aqueous isopropylamide, 5.0 g MAA (Rohm and Haas) and 20 g DI-$H_2O$ was metered in to the reactor over 60 minutes along with a solution of 0.5 g of $(NH_4)_2S_2O_8$ dissolved in 20 g of $H_2O$ which was metered in over 67 minutes. The initiator was pre-fed 2 minutes prior to the monomer feed and post-fed 5 minutes after the monomer feed was completed. The viscosity of the mixture gradually increased as the reaction proceeded. Following addition of the reagents, the mixture was held at 88° C. for 5 minutes, and a solution of 1.0 g of 0.15% FeSO4.$H_2O$ was added. Next, 0.25 g sodium bisulfite dissolved in 10 g DI-$H_2O$ and 0.25 g $(NH_4)_2S_2O_8$ dissolved in 10 g of $H_2O$ was added over 15 minutes. The mixture was cooled to room temperature and packaged. The hazy sample had polymer solids level of 20.2%, pH 2.8 and measured viscosity was 2980 cPs.

EXAMPLE 32

Gradual Addition Process, 65 N,N-Dimethylacrylamide/30 AMPS/5 MAA

The terpolymer was prepared by a gradual addition process. A one liter resin kettle with overhead stirrer, $N_2$ inlet, condenser, thermocouple, heating mantle, and provision for external cooling was set up in a hood. DI water (145 g) was charged to the kettle and heated to 88° C. under $N_2$. A mixture of 60 g of AMPS-sodium salt (51.2%, from Lubrizol), 130 g of 50% aqueous N,N-Dimethyl acrylamide, 5.0 g MAA (Rohm and Haas) and 20 g DI-$H_2O$ was metered in to the reactor over 60 minutes along with a solution of 0.5 g of $(NH_4)_2S_2O_8$ dissolved in 20 g of $H_2O$ which was metered in over 67 minutes. The initiator was pre-fed 2 minutes prior to the monomer feed and post-fed 5 minutes after the monomer feed was completed. The viscosity of the mixture gradually increased as the reaction proceeded. Following addition of the reagents, the mixture was held at 88° C. for 5 minutes, and a solution of 1.0 g of 0.15% FeSO4.$H_2O$ was added. Next, 0.25 g sodium bisulfite dissolved in 10 g DI-$H_2O$ and 0.25 g $(NH_4)_2S_2O_8$ dissolved in 10 g of $H_2O$ was added over 15 minutes. The mixture was cooled to room temperature and packaged. This resulted in a very high viscosity gel-like solution.

EXAMPLE 33

Gradual Addition Process, 65 AM/30 AMPS/5 EA

The terpolymer was prepared by a gradual addition process. A one liter resin kettle with overhead stirrer, $N_2$ inlet, condenser, thermocouple, heating mantle, and provision for external cooling was set up in a hood. DI water (145 g) was charged to the kettle and heated to 88° C. under $N_2$. A mixture of 60 g of AMPS-sodium salt (51.2%, from Lubrizol), 130 g of 50% aqueous acrylamide, 5.0 g ethylacrylate (Rohm and Haas) and 20 g DI-$H_2O$ was metered in to the reactor over 60 minutes along with a solution of 0.5 g of $(NH_4)_2S_2O_8$ dissolved in 20 g of $H_2O$ which was metered in over 67 minutes. The initiator was pre-fed 2 minutes prior to the monomer feed and post-fed 5 minutes after the monomer feed was completed. The viscosity of the mixture gradually increased as the reaction proceeded. Following addition of the reagents, the mixture was held at 88° C. for 5 minutes, and a solution of 1.0 g of 0.15% FeSO4.$H_2O$ was added. Next, 0.25 g sodium bisulfite dissolved in 10 g DI-$H_2O$ and 0.25 g $(NH_4)_2S_2O_8$ dissolved in 10 g of $H_2O$ was added over 15 minutes. The mixture was cooled to room temperature and packaged. Polymer solids were 26.3%, pH 2.9 and measured was viscosity 4320 cPs.

EXAMPLE 34

Gradual Addition Process, 65 AM/30 AMPS/5 MMA

The terpolymer was prepared by a gradual addition process. A one liter resin kettle with overhead stirrer, $N_2$ inlet, condenser, thermocouple, heating mantle, and provision for external cooling was set up in a hood. DI water (161 g) was charged to the kettle and heated to 88° C. under $N_2$. A mixture of 60 g of AMPS-sodium salt (51.2%, from Lubrizol), 130 g of 50% aqueous acrylamide, 5.0 g methylmethacrylate (Rohm and Haas) and 20 g DI-$H_2O$ was metered in to the reactor over 60 minutes along with a solution of 0.5 g of $(NH_4)_2S_2O_8$ dissolved in 20 g of $H_2O$ which was metered in over 67 minutes. The initiator was pre-fed 2 minutes prior to the monomer feed and post-fed 5 minutes after the monomer feed was completed. The viscosity of the mixture gradually increased as the reaction proceeded. Following addition of the reagents, the mixture was held at 88° C. for 15 minutes, then cooled to 70° C. Next, 0.25 g sodium bisulfite dissolved in 10 g DI-$H_2O$ and 0.25 g $(NH_4)_2S_2O_8$ dissolved in 10 g of $H_2O$ was added over 15 minutes. The mixture was held at 70° C. 15 minutes more, then cooled to room temperature and packaged. Polymer solids were 26.7%, pH 3.2 and measured viscosity 2940 cPs.

EXAMPLE 35

Gradual Addition Process, 65 AM/30 AMPS/5 DMAEMA

The terpolymer was prepared by a gradual addition process. A one liter resin kettle with overhead stirrer, $N_2$ inlet, condenser, thermocouple, heating mantle, and provision for external cooling was set up in a hood. DI water (161 g) was charged to the kettle and heated to 88° C. under $N_2$. A mixture of 60 g of AMPS-sodium salt (51.2%, from Lubrizol), 130 g of 50% aqueous acrylamide, 5.0 g N,N-dimethylaminoethyl methacrylate (Rohm and Haas) and 8 g DI-$H_2O$ was metered in to the reactor over 60 minutes along with a solution of 0.5 g of $(NH_4)_2S_2O_8$ dissolved in 20 g of $H_2O$ which was metered in over 67 minutes. The initiator was pre-fed 2 minutes prior to the monomer feed and post-fed 5 minutes after the monomer feed was completed. The viscosity of the mixture gradually increased as the reaction proceeded. Following addition of the reagents the mixture was held at 88° C. for 15 minutes, then cooled to 70° C. Next, 0.22 g sodium bisulfite dissolved in 10 g DI-$H_2O$ and 0.22 g $(NH_4)_2S_2O_8$ dissolved in 10 g of $H_2O$ was added over 15 minutes. The mixture was held at 70° C. 15 minutes more, then cooled to room temperature and packaged. Polymer solids were 27.8%, pH 8.95 and measured viscosity was 3100 cPs.

EXAMPLE 36

Modified Shot Process, 60 AM/40 AMPS

The copolymer was prepared by a modified shot addition process. A one liter resin kettle with overhead stirrer, $N_2$ inlet, condenser, thermocouple, heating mantle, and provision for external cooling was set up in a hood. DI water (125 g) along with 101.7 g of AMPS-sodium salt (50.5%, from Lubrizol) was charged to the kettle. Next, 154.2 g of 50% aqueous acrylamide from Cytec followed by 0.051 g of $CuCl_2$ dissolved in 77.6 g DI water was added and the mixture was heated to 50° C. under $N_2$ with stirring. The heating mantle was removed and 0.65 g of $(NH_4)_2S_2O_8$ dissolved in 31 ml of $H_2O$ was added. Within 2 minutes the exotherm started, the solution became thicker, and the $N_2$ flow was reduced and removed to the head space. The exotherm peaked at 92° C. twenty-five minutes after the initiator addition. After completion of the exotherm, a temperature of 85° C. was maintained for 30 minutes with constant stirring. A sample was removed for acrylamide and MW analysis. Sodium bisulfite (0.77 g dissolved in 45 g DI water) was added. After stirring for an hour, vacuum was pulled for 1–3 minutes several times over about a 15 minute period to help remove excess $SO_2$. The reaction mixture was then cooled and packaged. Polymer solids were 26.9%.

EXAMPLE 37

Gradual Addition Process, Polyacrylamide

The homopolymer was prepared by a gradual addition process. A one liter resin kettle with overhead stirrer, $N_2$ inlet, condenser, thermocouple, heating mantle, and provision for external cooling was set up in a hood. DI water (145 g) was charged to the kettle and heated to 88° C. under $N_2$. A solution of 200 g of 50% aqueous acrylamide was metered in to the reactor over 60 minutes along with a solution of 0.5 g of $(NH_4)_2S_2O_8$ dissolved in 20 g of $H_2O$ which was metered in over 67 minutes. The initiator was pre-fed 2 minutes prior to the monomer feed and post-fed 5 minutes after the monomer feed was completed. The viscosity of the mixture gradually increased as the reaction proceeded. Following addition of the reagents, the mixture was held at 88° C. for 5 minutes. Next, 0.2 g sodium bisulfite dissolved in 10 g DI-$H_2O$ and 0.2 g $(NH_4)_2S_2O_8$ dissolved in 10 g of $H_2O$ was added over 15 minutes. The mixture was cooled to room temperature and packaged. Polymer solids was 23.6%, pH 2.7 and measured viscosity was 27,400 cPs.

EXAMPLE 38

Gradual Addition Process, Poly AMPS

The homopolymer was prepared by a gradual addition process. A one liter resin kettle with overhead stirrer, $N_2$ inlet, condenser, thermocouple, heating mantle, and provision for external cooling was set up in a hood. DI water (161 g) was charged to the kettle and heated to 88° C. under $N_2$. A solution of 200 g of AMPS-sodium salt (51.2%, from Lubrizol) was metered in to the reactor over 60 minutes along with a solution of 0.5 g of $(NH_4)_2S_2O_8$ dissolved in 20 g of $H_2O$ which was metered in over 67 minutes. The initiator was pre-fed 2 minutes prior to the monomer feed and post-fed 5 minutes after the monomer feed was completed. The viscosity of the mixture gradually increased as the reaction proceeded. Following addition of the reagents, the mixture was held at 88° C. for 5 minutes. Next, 0.2 g sodium bisulfite dissolved in 10 g DI-$H_2O$ and 0.2 g $(NH_4)_2S_2O_8$ dissolved in 10 g of $H_2O$ was added over 15 minutes. The mixture was cooled to room temperature and packaged. Polymer solids were 26.2%, pH 4.4 and measured viscosity was 36 cPs.

Using the gradual addition process of the invention, a wide range of polymers are prepared having a range of solution viscosities, Mw and Mn as summarized in Table 1.

TABLE 1

Polymers prepared by gradual addition.

| Sample | Composition | Solids (%) | Solution Viscosity (cPs) | Mw | Mn |
|---|---|---|---|---|---|
| 29 | 65 AM/30 AMPS/5 MAA | 26.4 | 1440 | 218,000 | 33,000 |
| 30 | 65 Methacrylamide/30 AMPS/5 MAA | 20.1 | 250 | 107,000 | 14,800 |
| 31 | 65 N-Isopropyl AM/30 AMPS/5 MAA | 20.2 | 2980 | | |
| 32 | 65 N,N-Dimethyl AM/30 AMPS/5 MAA | 20.4 | | | |
| 33 | 65 AM/30 AMPS/5 EA | 26.3 | 4320 | 322,000 | 26,700 |
| 34 | 65 AM/30 AMPS/5 MMA | 26.7 | 2940 | 323,000 | 34,100 |
| 35 | 65 AM/30 AMPS/5 DMAEMA | 27.8 | 3100 | 361,000 | 42,200 |
| 36 | 65 AM/30 AMPS/5 MAPTAC | 25.9 | 2960 | 326,000 | 25,000 |
| 37 | Poly AM | 23.6 | 27,400 | 91,200 | 9,100 |
| 38 | Poly AMPS | 26.2 | 36 | 36,900 | 7,000 |

General Procedure for Staggered Feeds

EXAMPLE 39

Staggered Gradual Addition, 65 AM/35 AMPS

A one liter resin kettle with overhead stirrer, $N_2$ inlet, condenser, thermocouple, heating mantle, and provision for external cooling was set up in a hood. DI water (145 g) was charged to the kettle and heated to 88° C. under $N_2$. Three separate feed streams were utilized consisting of 70 g of 50% AMPS-sodium salt (from Lubrizol), 130 g of 50% aqueous acrylamide (from Cytec), and 0.5 g of $(NH_4)_2S_2O_8$ dissolved in 20 g of $H_2O$.

Initiator and Monomer A streams were started first, followed by Monomer B X minutes later. The Monomer B feed was completed X minutes before the Monomer A feed. The initiator was metered in over a total of 65 minutes, Monomer A over 60 minutes and Monomer B over 60–2X minutes). Following completion of all feed streams, the mixture was held at 88° C. for 5 minutes. Next, 0.2 g sodium bisulfite dissolved in 10 g DI-$H_2O$ and 0.20 g $(NH_4)_2S_2O_8$ dissolved in 10 g of $H_2O$ was added over 15 minutes with cooling.

Using the staggered gradual addition process of the invention, a wide range of solution viscosities, Mw and Mn is obtained for polymers having the same composition, as summarized in Table 2.

TABLE 2

Polymers prepared by staggered gradual addition.

| Composition (Weight %) | | | | Solution | | |
|---|---|---|---|---|---|---|
| Monomer A | Monomer B | X (min.) | Solids (%) | Viscosity (cPs) | Mw | Mn |
| 65 AM | 35 AMPS | 2 | 25.5 | 5,920 | 369,000 | 40,100 |
| 65 AM | 35 AMPS | 5 | 25.4 | 12,700 | 417,000 | 45,200 |
| 65 AM | 35 AMPS | 10 | 25.4 | 5,020 | 307,000 | 28,500 |
| 65 AM | 35 AMPS | 20 | 25.4 | 14,550 | 312,000 | 24,300 |
| 35 AMPS | 65 AM | 2 | 25.8 | 3,400 | 312,000 | 28,100 |
| 35 AMPS | 65 AM | 5 | 25.8 | 12,000 | 380,000 | 33,600 |
| 35 AMPS | 65 AM | 10 | 25.8 | 19,000 | 407,000 | 38,400 |
| 35 AMPS | 65 AM | 20 | 25.5 | 31,650 | 479,000 | 29,000 |

Comparative Example for Hybrid Process (Shot Process, 60 AM/40 AMPS).

A one liter resin kettle with overhead stirrer, $N_2$ inlet, condenser, thermocouple, heating mantle, and provision for external cooling was set up in a hood. DI water (125 g) along with 101.7 g of AMPS-sodium salt (50.5%, from Lubrizol) was charged to the kettle. Next, 154.2 g of 50% aqueous acrylamide from Cytec followed by 0.051 g of $CuCl_2$ dissolved in 77.6 g DI water was added and the mixture was heated to 50° C. under $N_2$ with stirring. The heating mantle was removed and 0.65 g of $(NH_4)_2S_2O_8$ dissolved in 31 ml of $H_2O$ was added. Within 2 minutes the exotherm started, the solution became thicker, and the $N_2$ flow was reduced and removed to the head space. The exotherm peaked at 92° C. twenty-five minutes after the initiator addition. After completion of the exotherm, a temperature of 85° C. was maintained for 30 minutes with constant stirring. A sample was removed for acrylamide and MW analysis. Sodium bisulfite (0.77 g dissolved in 45 g DI water) was added. After stirring for an hour, vacuum was pulled for 1–3 minutes several times over about a 15 minute period to help remove excess $SO_2$. The reaction mixture was then cooled and packaged. Polymer solids were 26.9% and measured viscosity was 45,100 cPs.

Comparative for Hybrid Process Example 29 (Grad. Add., 65 AM/30 AMPS/5 MAA).

A one liter resin kettle with overhead stirrer, $N_2$ inlet, condenser, thermocouple, heating mantle, and provision for external cooling was set up in a hood. DI water (146 g) was charged to the kettle and heated to 90° C. under $N_2$. 20.3 grams of monomer mixture consisting of 60 g of AMPS-sodium salt (50%, from Lubrizol), 130 g of 50% aqueous acrylamide, 5.0 g methylmethacrylate (Rohm and Haas) and 8 g DI-$H_2O$ was pre-charged to the kettle followed by 2 grams of initiator solution (0.5 g of APS dissolved in 20 g of $H_2O$). After 5 minutes, the remaining monomer mixture was metered in to the reactor over 60 minutes along with the remaining initiator which was metered in over 67 minutes. The initiator was pre-fed 2 minutes prior to the monomer feed and post-fed 5 minutes after the monomer feed was completed. The viscosity of the mixture gradually increased as the reaction proceeded. Following addition of the reagents, the mixture was held at 88° C. for 15 minutes, then cooled to 70° C. Next, 0.22 g sodium bisulfite dissolved in 11 g DI-$H_2O$ and 0.22 g $(NH_4)_2S_2O_8$ dissolved in 11 g of $H_2O$ was added over 15 minutes. The mixture was held at 70° C. 15 minutes more, then cooled to room temperature and packaged. Polymer solids were 26.0%, pH 4.7 and measured viscosity was 2630 cPs.

EXAMPLE 40

Hybrid Process, 65 AM/30 AMPS/5 MAA

A one liter resin kettle with overhead stirrer, $N_2$ inlet, condenser, thermocouple, heating mantle, A one liter resin kettle with overhead stirrer, $N_2$ inlet, condenser, thermocouple, heating mantle, and provision for external cooling was set up in a hood. DI water (146 g) was charged to the kettle and heated to 90° C. under $N_2$. 40.6 grams of monomer mixture consisting of 60 g of AMPS-sodium salt (50%, from Lubrizol), 130 g of 50% aqueous acrylamide, 5.0 g methylmethacrylate (Rohm and Haas) and 8 g DI-$H_2O$ was pre-charged to the kettle followed by 4 grams of initiator solution (0.5 g of APS dissolved in 20 g of $H_2O$). A 3° C. exotherm was noted. After 5 minutes, the remaining monomer mixture was metered in to the reactor over 60 minutes along with the remaining initiator which was metered in over 67 minutes. The initiator was pre-fed 2 minutes prior to the monomer feed and post-fed 5 minutes after the monomer feed was completed. The viscosity of the mixture gradually increased as the reaction proceeded. Following addition of the reagents, the mixture was held at 88° C. for 15 minutes, then cooled to 70° C. Next, 0.22 g sodium bisulfite dissolved in 11 g DI-$H_2O$ and 0.22 g $(NH_4)_2S_2O_8$ dissolved in 11 g of $H_2O$ was added over 15 minutes. The mixture was held at 70° C. 15 minutes more, then cooled to room temperature and packaged. Polymer solids were 26.6%, pH 4.8 and measured viscosity was 2130 cPs.

(Hybrid Process, 65 AM/30 AMPS/5 MAA).

A one liter resin kettle with overhead stirrer, $N_2$ inlet, condenser, thermocouple, heating mantle, A one liter resin kettle with overhead stirrer, $N_2$ inlet, condenser, thermocouple, heating mantle, and provision for external cooling was set up in a hood. DI water (146 g) was charged to the kettle and heated to 90° C. under $N_2$. 60.9 grams of monomer mixture consisting of 60 g of AMPS-sodium salt (50%, from Lubrizol), 130 g of 50% aqueous acrylamide, 5.0 g methylmethacrylate (Rohm and Haas) and 8 g DI-$H_2O$ was pre-charged to the kettle followed by 1.95 grams of initiator solution (0.5 g of APS dissolved in 20 g of $H_2O$). A 3° C. exotherm was noted. After 5 minutes, the remaining monomer mixture was metered in to the reactor over 60 minutes along with the remaining initiator which was metered in over 67 minutes. The initiator was pre-fed 2 minutes prior to the monomer feed and post-fed 5 minutes after the monomer feed was completed. The viscosity of the mixture gradually increased as the reaction proceeded. Following addition of the reagents, the mixture was held at 88° C. for 15 minutes, then cooled to 70° C. Next, 0.22 g sodium bisulfite dissolved in 11 g DI-H$_2$O and 0.22 g (NH$_4$)$_2$S$_2$O$_8$ dissolved in 11 g of H$_2$O was added over 15 minutes. The mixture was held at 70° C. 15 minutes more, then cooled to room temperature and packaged. Polymer solids were 28.6%, pH 4.9 and measured viscosity was 3580 cPs.

(Hybrid Process, 65 AM/30 AMPS/5 MAA).

A one liter resin kettle with overhead stirrer, N$_2$ inlet, condenser, thermocouple, heating mantle, A one liter resin kettle with overhead stirrer, N$_2$ inlet, condenser, thermocouple, heating mantle, and provision for external cooling was set up in a hood. DI water (146 g) was charged to the kettle and heated to 90° C. under N$_2$. 81.2 grams of monomer mixture consisting of 60 g of AMPS-sodium salt (50%, from Lubrizol), 130 g of 50% aqueous acrylamide, 5.0 g methylmethacrylate (Rohm and Haas) and 8 g DI-H$_2$O was pre-charged to the kettle followed by 0.98 grams of initiator solution (0.5 g of APS dissolved in 20 g of H$_2$O). A 3° C. exotherm was noted. After 5 minutes, the remaining monomer mixture was metered in to the reactor over 60 minutes along with the remaining initiator which was metered in over 67 minutes. The initiator was pre-fed 2 minutes prior to the monomer feed and post-fed 5 minutes after the monomer feed was completed. The viscosity of the mixture gradually increased as the reaction proceeded. Following addition of the reagents, the mixture was held at 88° C. for 15 minutes, then cooled to 70° C. Next, 0.22 g sodium bisulfite dissolved in 11 g DI-H$_2$O and 0.22 g (NH$_4$)$_2$S$_2$O$_8$ dissolved in 11 g of H$_2$O was added over 15 minutes. The mixture was held at 70° C. 15 minutes more, then cooled to room temperature and packaged. Polymer solids were 28.5%, pH 4.9 and measured viscosity was 9150 cPs.

(Hybrid Process, 65 AM/30 AMPS/5 MAA).

A one liter resin kettle with overhead stirrer, N$_2$ inlet, condenser, thermocouple, heating mantle, A one liter resin kettle with overhead stirrer, N$_2$ inlet, condenser, thermocouple, heating mantle, and provision for external cooling was set up in a hood. DI water (146 g) was charged to the kettle and heated to 90° C. under N$_2$. 101.5 grams of monomer mixture consisting of 60 g of AMPS-sodium salt (50%, from Lubrizol), 130 g of 50% aqueous acrylamide, 5.0 g methylmethacrylate (Rohm and Haas) and 8 g DI-H$_2$O was pre-charged to the kettle followed by 0.98 grams of initiator solution (0.5 g of APS dissolved in 20 g of H$_2$O). A 1° C. exotherm was noted. After 5 minutes, the remaining monomer mixture was metered in to the reactor over 60 minutes along with the remaining initiator which was metered in over 67 minutes. The initiator was pre-fed 2 minutes prior to the monomer feed and post-fed 5 minutes after the monomer feed was completed. The viscosity of the mixture gradually increased as the reaction proceeded. Following addition of the reagents, the mixture was held at 88° C. for 15 minutes, then cooled to 70° C. Next, 0.22 g sodium bisulfite dissolved in 11 g DI-H$_2$O and 0.22 g (NH$_4$)$_2$S$_2$O$_8$ dissolved in 11 g of H$_2$O was added over 15 minutes. The mixture was held at 70° C. 15 minutes more, then cooled to room temperature and packaged. Polymer solids were 30.5%, pH 4.9 and measured viscosity was 21,150 cPs.

(Hybrid Process, 65 AM/30 AMPS/5 MAA).

A one liter resin kettle with overhead stirrer, N$_2$ inlet, condenser, thermocouple, heating mantle, A one liter resin kettle with overhead stirrer, N$_2$ inlet, condenser, thermocouple, heating mantle, and provision for external cooling was set up in a hood. DI water (146 g) was charged to the kettle and heated to 90° C. under N$_2$. 101.5 grams of monomer mixture consisting of 60 g of AMPS-sodium salt (50%, from Lubrizol), 130 g of 50% aqueous acrylamide, 5.0 g methylmethacrylate (Rohm and Haas) and 8 g DI-H$_2$O was pre-charged to the kettle followed by 1.96 grams of initiator solution (0.5 g of APS dissolved in 20 g of H$_2$O). A 8° C. exotherm was noted. After 5 minutes, the remaining monomer mixture was metered in to the reactor over 60 minutes along with the remaining initiator which was metered in over 67 minutes. The initiator was pre-fed 2 minutes prior to the monomer feed and post-fed 5 minutes after the monomer feed was completed. The viscosity of the mixture gradually increased as the reaction proceeded. Following addition of the reagents, the mixture was held at 88° C. for 15 minutes, then cooled to 70° C. Next, 0.22 g sodium bisulfite dissolved in 11 g DI-H$_2$O and 0.22 g (NH$_4$)$_2$S$_2$O$_8$ dissolved in 11 g of H$_2$O was added over 15 minutes. The mixture was held at 70° C. 15 minutes more, then cooled to room temperature and packaged. Polymer solids were 31.3%, pH 4.9 and measured viscosity was 15,550 cPs.

Example 40 illustrates the effects of the hybrid process of the invention on a terpolymer composition 65AM/30AMPS™/5MAA as compared to a shot addition and a gradual addition, as summarized in Table 3. The hybrid process increases Mw without a significant increase in solution viscosity as compared to gradual addition or shot addition.

TABLE 3

Effects of Hybrid process versus Shot Addition or Gradual Addition for 65 AM/35 AMPS ™ /5MAA polymer composition.

| Process Description | Solids (%) | Solution Viscosity (cPs) | Mw | Mn |
|---|---|---|---|---|
| Shot- add initiator to total monomer charge in reactor; nothing metered in | 26.9 | 45,100 | 416,000 | 48,000 |
| Gradual Addition- No pre-charge. All monomer and initiator metered into reactor over time. | 26.4 | 1440 | 218,000 | 33,000 |
| Hybrid- 10% monomer and initiator pre-charged to reactor. The rest is metered in | 26.0 | 2630 | 291,000 | 37,400 |
| Hybrid- 20% monomer and initiator pre-charged to reactor. The rest is metered in | 26.6 | 2130 | 278,000 | 34,200 |
| Hybrid- 30% monomer and 10% initiator pre-charged to reactor. The rest is metered in | 29.6 | 3580 | 320,000 | 32,600 |

TABLE 3-continued

Effects of Hybrid process versus Shot Addition or Gradual Addition for 65 AM/35 AMPS™ /5MAA polymer composition.

| Process Description | Solids (%) | Solution Viscosity (cPs) | Mw | Mn |
|---|---|---|---|---|
| Hybrid- 40% monomer and 5% initiator pre-charged to reactor. The rest is metered in | 28.5 | 9150 | 396,000 | 35,800 |
| Hybrid- 50% monomer and 5% initiator pre-charged to reactor. The rest is metered in | 30.5 | 21,150 | 453,000 | 33,000 |
| Hybrid- 50% monomer and 10% initiator pre-charged to reactor. The rest is metered in | 31.3 | 15,550 | 449,000 | 42,500 |

EXAMPLE 41

Redox Initiated Process

A one liter resin kettle with overhead stirrer, $N_2$ inlet, condenser, thermocouple, heating mantle, and provision for external cooling was set up in a hood. DI water (125 g) along with 66.95 g of AMPS™-sodium salt (50%, from Lubrizol) and 179.69 g of 52.7% aqueous acrylamide from Cytec was charged to the kettle under $N_2$ with stirring. A solution of 0.39 g of Lykopon dissolved in 20 g of $H_2O$ was added to the kettle and allowed to stir for 15 mins. The mantle was removed and a solution of 0.65 g of $(NH_4)_2S_2O_8$ dissolved in 31 ml of $H_2O$ was added. Within 1 minute the exotherm started, the solution became thicker, and the $N_2$ flow was reduced and removed to the head space. The exotherm peaked at 73° C. three minutes after the initiator addition. After completion of the exotherm, a temperature of 73° C. was maintained for 45 minutes with constant stirring. Sodium bisulfite (0.77 g dissolved in 45 g DI water) was added. After stirring for 60 minutes at 73° C., the reaction mixture was vacuum stripped periodically over 30 mins. The reaction was then cooled and packaged. Polymer solids were 29.29% and measured viscosity was 11,300 cPs.

EXAMPLE 42

Shot Process at High Dilution with AMPS Free Acid

A one liter resin kettle with overhead stirrer, $N_2$ inlet, condenser, thermocouple, heating mantle, and provision for external cooling was set up in a hood. DI water (300 g) along with 25.7 g of AMPS™ was charged to the kettle. Next, 72.73 g of 53% aqueous acrylamide from Cytec followed by 0.026 g of $CuCl_2$ dissolved in 10 g DI water was added and the mixture was heated to 40° C. under $N_2$ with stirring. The heating mantle was removed and 0.325 g of $(NH_4)_2S_2O_8$ dissolved in 10 ml of $H_2O$ was added. With no observable exotherm after 15 minutes, the reaction was heated to 45° C. After 15 minutes and no exotherm, the reaction was heated to 50° C. Within 7 minutes the exotherm started, the solution became thicker, and the $N_2$ flow was reduced and removed to the head space. The exotherm peaked at 60° C. within twenty five minutes. After completion of the exotherm, a temperature of 60° C. was maintained for 30 minutes with constant stirring. Sodium bisulfite (0.16 g dissolved in 10 g DI water) was added and held for twenty minutes. The sodium bisulfite addition was repeated and held for twenty minutes. Samples were periodically removed for acrylamide and MW analysis. The reaction mixture was then cooled and packaged. Polymer solids were 14.9% and measured viscosity was 30,800 cPs.

EXAMPLE 43

Gradual Addition Process with AMPS Free Acid

A one liter resin kettle with overhead stirrer, $N_2$ inlet, condenser, thermocouple, heating mantle, and inlets for the addition of monomers and initiators, and provision for external cooling was set up in a hood. DI water (120 g) was charged to the kettle and heated to 88° C. under $N_2$ with stirring. A solution of 51.4 g of AMPS™ and 60 g $H_2O$ was prepared. 145.5 g of 53% aqueous acrylamide from Cytec was added to an addition vessel and a solution of 0.65 g of $(NH_4)_2S_2O_8$ dissolved in 100 ml of $H_2O$ was prepared. At 88° C., the monomers and initator solution were added to the kettle over 90 minutes. At the completition of the feeds the reaction mixture was held for thirty minutes. Sodium bisulfite (0.5 g dissolved in 40 g DI water) was added and held for thirty minutes with constant stirring. Samples were periodically removed for acrylamide and MW analysis. The reaction mixture was then cooled and packaged. Polymer solids were 25.25% and measured viscosity was 9,320 cPs.

EXAMPLE 44

Hybrid with Vaso-50 Initiator

A one liter resin kettle with overhead stirrer, $N_2$ inlet, condenser, thermocouple, heating mantle, A one liter resin kettle with overhead stirrer, $N_2$ inlet, condenser, thermocouple, heating mantle, and provision for external cooling was set up in a hood. DI water (1706 g) was charged to the kettle and heated to 88° C. under $N_2$. 24.75 grams of monomer mixture consisting of 102.8 g of AMPS-sodium salt (50%, from Lubrizol), and 144.68 g of 53% aqueous acrylamide (from Cytec), was pre-charged to the kettle followed by 6.07 grams of initiator solution (0.77 g of Vaso-50 dissolved in 60 g of $H_2O$). A 2° C. exotherm was noted. The remaining monomer mixture and initiator was metered in to the reactor over 90 minutes. The viscosity of the mixture gradually increased as the reaction proceeded. Following addition of the reagents, the mixture was held at 88° C. for 30 minutes, then cooled to room temperature and packaged. Polymer solids were 25.43% and measured viscosity was 2,900 cPs.

EXAMPLE 45

Modified Shot Process, Initiation at 40° C., 80 AM/20 AMPS

A one liter resin kettle with overhead stirrer, $N_2$ inlet, condenser, thermocouple, heating mantle, and provision for external cooling was set up in a hood. DI water (170 g) along with 51.4 g of AMPS-sodium salt (50.5%, from Lubrizol) was charged to the kettle. Next, 195.06 g of 50% aqueous acrylamide from Cytec followed by 0.051 g of $CuCl_2$ dissolved in 77.6 g DI water was added and the mixture was heated to 40° C. under $N_2$ with stirring. The heating mantle was removed and 0.65 g of $(NH_4)_2S_2O_8$ dissolved in 31 ml of $H_2O$ was added. Within 5 minutes the exotherm started, the solution became thicker, and the $N_2$ flow was reduced and removed to the head space. The exotherm peaked at 82° C. fifteen minutes after the initiator addition. After completion of the exotherm, a temperature of 82° C. was maintained for 60 minutes with constant stirring. Samples were periodically removed for acrylamide and MW analysis. The reaction mixture was then cooled and packaged. Polymer solids were 25.6%.

Examples 41–45 demonstrate how other process variants of the invention affect polymer molecular weight distribution, structure and viscosity as compared to conventional gradual addition and shot addition processes. Results are summarized in Table 4. Use of other process variants provides high Mw solution polymers without high solution viscosity and raises Mn while controlling high Mw tailing. Any other variations and optimizations are within the scope of the invention.

comparable to commercially available hair treatments incorporating different polymers (Comparative Examples 3 and 4). Addition of small amounts of acid-containing monomers including AA and MAA to AM/AMPS™ copolymers results also in unexpected formulation clarity (Examples 21–27). The invented multi-functional solution polymers in the hair fixative formulation exhibit an excellent balance of water resistance versus water sensitivity. In addition, the invented polymers exhibit good color stability and good water stabilities and the polymers are non-flaking after application to hair. One advantage of the invented polymers is that the polymers are compatible when combined with additives including neutralizers, surfactants and thickeners. Moreover, addition of small of acid-containing monomers provides hair formulations that are compatible with thickeners such as carbomers, including Carbopol and result in hair formulations having stable formulation viscosities as shown in Table 1. Another advantage of the invented polymers is that the polymers can be neutralized at any stage of preparing the formulation, which is not true of copolymers known in the prior art.

The polymers of the present invention have numerous advantages over polymers described in U.S. Pat. Nos. 6,569,413; 4,859,458; 4,578,267; and 4,401,650. All prior art publications describe AM/AMPS™ (also known as Lubrizol™) copolymers neutralized with basic compounds, including base addition salts and ethoxylated fatty amines. Polymers of the invention differ significantly as compared with prior art copolymers in terms of their molecular weight distributions, polymer morphology, polymer properties and the process by which they are prepared. Polymers prepared

TABLE 4

Effects of other process variants on for AMPS/AM copolymer.

| Example | Process Description | Solids (%) | Solution Viscosity (cPs) | Mw | Mn | PDI Mw/Mn |
|---|---|---|---|---|---|---|
|  | Shot- add initiator to total monomer charge in reactor; nothing metered in | 26.9 | 45,100 | 416,000 | 48,000 | 8.7 |
| 29 | Gradual Addition- No pre-charge. All monomer and initiator metered into reactor over time. | 26.4 | 1440 | 218,000 | 33,000 | 6.6 |
| 40 | Hybrid- 50% monomer and 10% initiator pre-charged to reactor. The rest is metered in | 31.3 | 15,550 | 449,000 | 42,500 | 10.6 |
| 41 | Redox initiated shot process Hold for redox grad-add example | 29.3 | 11,300 | 198,000 | 20,400 | 9.7 |
| 42 | Shot process at high dilution with AMPS free acid | 14.9 | 30,800 | 895,000 | 505,000 | 1.8 |
| 43 | Shot process with AMPS free acid | 25.2 | 9,320 | 578,000 | 105,000 | 5.5 |
| 44 | Gradual addition with organic initiator (V-50) | 25.4 | 2,900 | 295,000 | 47,000 | 6.3 |
| 45 | Shot process | 25.6 |  | 789,000 | 420,000 | 1.9 |

AM/AMPS™ copolymers incorporated in the hair formulation (Examples 1–13) are not clear (Comparative Example 1) and range from very hazy (Example 8) to slightly hazy (Examples 4, 6, 7, 12 and 13). Terpolymers of AM/acem/AMPS™ also provide unexpectedly clear hair formulations when the formulations are comprise the invented polymers (Examples 14–16 and 18–20). Moreover, the clarity is according to and described in the latter three publications are good hair conditioners, but are poor hair fixatives. The compatibility of polymers of the invention in thickeners including polycarboxylic acids, polyacrylic acids and carbomers including Carbopol™ is better than comparable anionic copolymers, such as MAA/AMPS™ and AM/AMPS™ copolymers.

We claim:
1. A process for preparing a polymer composition comprising the step of: (a) preparing a copolymer comprising, as polymerized monomer units, (i) 50 to 89.9 weight percent of one or more ethylenically unsaturated monomers and (ii) 10 to 40 weight percent of 2-acrylamido-2-methyl-1-propanesulfonic acid and salts thereof; by varying addition of monomers (i) and (ii) with respect to time and each monomer prior to neutralizing the polymer with a base.

* * * * *